(12) United States Patent
Makishima et al.

(10) Patent No.: US 9,018,194 B2
(45) Date of Patent: Apr. 28, 2015

(54) VITAMIN D RECEPTOR MODULATORS WITH PARTIAL AGONIST ACTIVITY

(75) Inventors: Makoto Makishima, Tokyo (JP); Sachiko Yamada, Tokyo (JP); Antonio Mourino, Ames (ES); Hiroaki Tokiwa, Tokyo (JP); Takeru Kudo, Tokyo (JP); Yusuke Watarai, Tokyo (JP); Kazuki Maekawa, Tokyo (JP)

(73) Assignees: Nibon University, Tokyo (JP); Rikkyo Gakuin, Tokyo (JP)

( * ) Notice: Subject to any disclaimer, the term of this patent is extended or adjusted under 35 U.S.C. 154(b) by 0 days.

(21) Appl. No.: 14/002,502

(22) PCT Filed: Mar. 1, 2012

(86) PCT No.: PCT/JP2012/055254
§ 371 (c)(1),
(2), (4) Date: Oct. 22, 2013

(87) PCT Pub. No.: WO2012/118154
PCT Pub. Date: Sep. 7, 2012

(65) Prior Publication Data
US 2014/0038925 A1    Feb. 6, 2014

(30) Foreign Application Priority Data
Mar. 2, 2011  (JP) ................. 2011-045022

(51) Int. Cl.
*A61K 31/593* (2006.01)
*C07C 401/00* (2006.01)

(52) U.S. Cl.
CPC .......... *C07C 401/00* (2013.01); *C07C 2101/14* (2013.01); *C07C 2102/24* (2013.01); *C07C 2103/74* (2013.01)

(58) Field of Classification Search
CPC ............................. C07C 401/00; A61K 31/593
USPC .......................................... 514/167; 552/653
See application file for complete search history.

(56) References Cited

U.S. PATENT DOCUMENTS
2006/0189576 A1    8/2006   Bouillon et al.

FOREIGN PATENT DOCUMENTS
JP        2005-247768 A        9/2005

OTHER PUBLICATIONS
International Search Report dated Apr. 24, 2012 for International Patent App. No. PCT/JP2012/055254 filed on Mar. 2, 2012.

Nakabayashi, et al., "Crystal Structures of Rat Vitamin D Receptor Bound to Adamantyl Vitamin D Analogs: Structural Basis for Vitamin D Receptor Antagonism and Partial Agonism", J. Med. Chem., 51:5320-5329. (2008).
European Patent Application No. 12752901.4, Supplementary European Search Report mailed on Jul. 17, 2014, 6 pages.
PCT International Application No. PCT/JP2012/055254, International Written Opinion mailed on Apr. 24, 2012, 5 pages of Official Language copy only.
PCT International Application No. PCT/JP2012/055254, International Preliminary Report on Patentability completed on Mar. 27, 2013, 10 pages (5 pages of English Translation and 5 pages of Official Copy).
Sicinski et al., "Synthesis and Biological Activity of 2-Hydroxy and 2-Alkoxy Analogs of 1.alpha.,25-Dihydroxy-19-norvitamin D3", Journal of Medicinal Chemistry, vol. 37, 1994, pp. 3730-3738.

*Primary Examiner* — Barbara P Badio
(74) *Attorney, Agent, or Firm* — Morgan, Lewis & Bockius LLP

(57) ABSTRACT

The present invention provides a compound which functions as a selective vitamin D receptor modulator and has action-selectivity or tissue-selectivity such that it does not induce hypercalcemia but causes other effects. There is provided a compound represented by formula (I), a solvate thereof or a prodrug thereof.

[Formula 1]

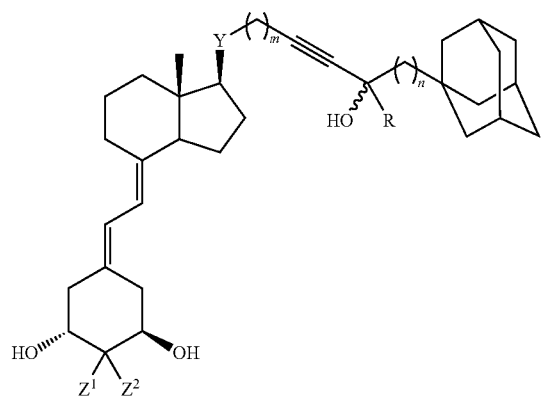

(I)

wherein m and n each independently represent 1 or 0;
R represents a hydrogen atom or an alkyl group;
Y represents an ethane-1,1-diyl group or an ethyne-1,2-diyl group; and
$Z^1$ represents a hydrogen atom and $Z^2$ represents a hydroxy-alkoxy group, or
$Z^1$ and $Z^2$ jointly form a methylene group.

3 Claims, 2 Drawing Sheets

Luciferase assay

VITAMIN D RECEPTOR MODULATORS WITH PARTIAL AGONIST ACTIVITY

TECHNICAL FIELD

The present invention relates to novel vitamin D receptor modulators with a partial agonist activity.

BACKGROUND ART

The active form of vitamin D exerts its functions (such as regulation of calcium metabolism, inhibition of cell proliferation/induction of differentiation, regulation of inflammation/immune response, regulation of the cardiovascular system and hair cycle, etc.) via binding to vitamin D receptor (VDR). If these activities can be controlled, it is believed that vitamin D preparations are potential therapeutics for osteoporosis, malignant neoplasms, infectious diseases, autoimmune diseases, cardiovascular diseases, alopecia and so forth.

However, most of those compounds which have been synthesized and developed as pharmaceuticals so far are agonists with action spectra almost similar to those of the natural hormone. They have the problem of hypercalcemia, an adverse effect common to active vitamin D preparations, and this has limited their development as pharmaceuticals. Among them, alfacalcidol was developed as the first therapeutic for osteoporosis; subsequently, maxacalcitol and calcipotriene were developed clinically as topical therapeutics for psoriasis. Maxacalcitol exhibits pharmacokinetic tissue-selectivity, and its clinical application has been expanded as a therapeutic for secondary hyperparathyroidism. However, vitamin D preparations which have cell- or tissue-selectivity at the gene expression level (such as seen in selective estrogen receptor modulators of estrogen receptors) have not been developed yet. Further, several groups of compounds have been reported as vitamin D derivatives with VDR antagonist effect (Non-Patent Documents Nos. 1-3), but pharmaceutical development of them has not succeeded. On the other hand, a group of compounds called "non-secosteroid" found in totally synthesized substances as compounds with the activity of active vitamin D are now being developed as selective VDR modulators (Non-Patent Documents Nos. 4-8).

Conventional active vitamin D derivatives have been developed as VDR full agonists. When administered to human or animals, these derivatives increase blood calcium levels at the dose level where they exhibit their therapeutic effect. It is believed that the cause of hypercalcemia is the induction of expression of a calcium transporter gene in the small intestinal mucosa. This adverse effect (hypercalcemia) makes it difficult to use conventional active vitamin D derivatives safely in clinical scenes for treating diseases other than vitamin D deficiency such as rickets or osteomalacia. This is the reason why active vitamin D preparations could not be developed as therapeutics for osteoporosis in Europe and the United States; and this is also the reason why the development of vitamin D preparations as anticancer agents or immunomodulatory agents did not succeed. Therefore, the key to the development of active vitamin D preparations is to separate the blood calcium raising effect (calcium absorption enhancement effect in the small intestinal mucosa) from other effects. To date, no success has been reported in this separation. One of the reasons is considered as follows: in VDR full agonist-type derivatives developed so far, the surface structure of the activation function 2 (AF2) of ligand-bound VDR is similar to those of the conventional VDR agonists, and, thus, no selectivity will occur in the binding to various coactivators, corepressors, etc. (which are transcriptional coactivators). As a result, their activity cannot be expected to have tissue-selectivity.

PRIOR ART LITERATURE

Non-Patent Documents

Non-Patent Document No. 1: Bury, Y.; Steinmeyer, A.; Carlberg, C. Structure activity relationship of carboxylic ester antagonists of the vitamin D3 receptor. Mol. Pharmacol. 2000 58, 1067-74.

Non-Patent Document No. 2: Miura, D.; Manabe, K.; Ozono, K.; Saito, M.; Gao, Q.; Norman, A. W.; Ishizuka, S. Antagonistic action of novel 1alpha,25-dihydroxyvitamin D3-26,23-lactone analogs on differentiation of human leukemia cells (HL-60) induced by 1alpha,25-dihydroxyvitamin D3. J. Biol. Chem. 1999 274, 16392-16399.

Non-Patent Document No. 3: Kato, Y.; Nakano, Y.; Sano, H.; Tanatani, A.; Kobayashi, H.; Shimazawa, R.; Koshino, H.; Hashimoto, Y.; Nagasawa, K. Synthesis of 1alpha,25-dihydroxyvitamin D3-26,23-lactams (DLAMs), a novel series of 1 alpha,25-dihydroxyvitamin D3 antagonist. Bioorg. Med. Chem. Lett. 2004 14, 2579-2583.

Non-Patent Document No. 4: Boehm M F et al., Chem Biol 6 (1999) 265-275.

Non-Patent Document No. 5: Ma Y, et al., J. Clin Inves, 116 (2006) 892-904.

Non-Patent Document No. 6: Hosoda S et al., Bioorg Med Chem, (2006) 5489-5502.

Non-Patent Document No. 7: Sato M, et al., J Bone Mineral Res, (2010) 1326-1336.

Non-Patent Document No. 8: Kashiwagi H, et al., Bioorg Med Chem, 19 (2011) 4721-4729.

DISCLOSURE OF THE INVENTION

Problem for Solution by the Invention

It is an object of the present invention to provide a compound having action-selectivity or tissue-selectivity such that it functions as a selective VDR modulator and does not induce hypercalcemia but cause other effects.

Means to Solve the Problem

The present inventors have created a novel vitamin D compound which functions as a VDR partial agonist. The key to the designing of such a VDR partial agonist is (i) the side chain structure of ligand and (ii) the change of AF2 conformation of VDR upon ligand binding. This has been achieved by introducing a bulky adamantane ring and a triple bond into a side chain of vitamin D.

Each of the 23-yn-25(or 26)-adamantyl compounds (ADTK1 through ADTK4) synthesized currently exhibited the expected partial agonist activity in transcription activation tests (FIG. 2). These results suggest that changes occurred in the structure of the ligand-dependent transcription activation (AF2) of those VDRs to which the above-described compounds bound. Briefly, these results suggest that the surface structure of AF2 site was altered from the conventional agonist-binding type and that the affinities of coactivators and corepressors to AF2 surface were also altered. Each of the currently synthesized compounds is characterized by having a considerably higher efficacy (40-72%) than the double-bond derivatives (10-15%) previously reported by the present inventors (M. Igarashi et al., Archives of Biochemistry and Biophysics 460 (2007) 240-253; J. Med. Chem. 2008, 51, 5320-5329). However, in the co-presence of 1,25(OH)$_2$D3, the currently synthesized compounds competitively inhibited the effect of the natural hormone and decreased its activity to the activities of these compounds; thus, it was also shown that these compounds have a weak antagonist activity. Briefly, a possibility was suggested that these compounds would function as selective VDR modulators and have action-selectivity or tissue-selectivity such that they would not induce hypercalcemia but cause other effects.

The present invention has been achieved based on these findings.

A summary of the present invention is described below.

(1) A compound represented by the following formula (I), a solvate thereof or a prodrug thereof:

[Formula 1]

(I)

wherein m and n each independently represent 1 or 0;
R represents a hydrogen atom or an alkyl group;
Y represents an ethane-1,1-diyl group or an ethyne-1,2-diyl group; and
$Z^1$ represents a hydrogen atom and $Z^2$ represents a hydroxyalkoxy group, or
$Z^1$ and $Z^2$ jointly form a methylene group.

(2) The compound, solvate thereof or prodrug thereof according to (1) above, wherein the compound represented by the formula (I) is selected from the group consisting of (25S)-25-(1-Adamantyl)-1α,25-dihydroxy-2-methylene23,23,24,24-tetradehydro-19,26,27-trinorvitamin $D_3$, (25R)-25-(1-Adamantyl)-1α,25-dihydroxy-2-methylene-23,23,24,24-tetradehydro-19,26,27-trinorvitamin $D_3$, (25R)-26-(1-Adamantyl)-1α,25-dihydroxy-2-methylene-23,23,24,24-tetradehydro-19,27-dinorvitamin $D_3$, (25S)-26-(1-Adamantyl)-1α,25-dihydroxy-2-methylene-23,23,24,24-tetradehydro-19,27-dinorvitamin $D_3$, (25R)-25-(1-Adamantyl)-1α,25-dihydroxy-2-methylene-20,20,22,22,23,23,24,24-octadehydro-19,21,26,27-tetranorvitamin $D_3$, (25S)-25-(1-Adamantyl)-1α,25-dihydroxy-2-methylene-20,20,22,22,23,23,24,24-octadehydro-19,21,26,27-tetranorvitamin $D_3$, (25R)-25-(1-Adamantyl)-1α,25-dihydroxy-2-methylene-23,23,24,24-tetradehydro-19,27-dinorvitamin $D_3$ and (25S)-25-(1-Adamantyl)-1α,25-dihydroxy-2-methylene23,23,24,24-tetradehydro-19,27-dinorvitamin $D_3$.

(3) A composition comprising the compound, solvate thereof or prodrug thereof according to (1) above.

(4) The composition according to (3) above for activating a vitamin D receptor.

(5) The composition according to (3) or (4) above, which is for use as a pharmaceutical.

(6) The composition according to (5) above for preventing and/or treating a disease in which a vitamin D receptor is involved.

(7) The composition according to (5) or (6) above for preventing and/or treating a disease selected from the group consisting of osteoporosis, malignant neoplasm, psoriasis vulgaris, autoimmune disease, infectious disease and neurodegenerative disease.

(8) A method for activating a vitamin D receptor, comprising treating the vitamin D receptor-containing cell, tissue, organ or animal individual with the compound, solvate thereof or prodrug thereof according to (1) above.

(9) A method for preventing and/or treating a disease in which a vitamin D receptor is involved, comprising administering to a subject a pharmaceutically effective amount of the compound, solvate thereof or prodrug thereof according to (1) above.

(10) The compound, solvate thereof or prodrug thereof according to (1) above, which is for use in activating a vitamin D receptor.

(9) The compound, solvate thereof or prodrug thereof according to (1) above, which is for use in preventing and/or treating a disease in which a vitamin D receptor is involved.

In the development of VDR agonists, it is not important to search for potent agonists. The present inventors converted such an orientation in the development and designed those compounds which would intentionally alter the structure of VDR activating surface (AF2 surface). As a result, it was predicted that those compounds having a certain degree of hindrance in the binding of coactivators would not exhibit the activity of a full agonist like the natural hormone. The results of a transcription activation assay revealed that the thus designed compounds of the present invention exhibit a partial agonist activity as predicted.

Therefore, it is predicted that the transcription activity of these compounds will change depending on the concentrations of transcriptional coactivators in the target cell. In other words, it can be said that these compounds are potential tissue-selective VDR modulators.

Effect of the Invention

Since the compound of the present invention exhibits a VDR partial agonist activity, the compound is capable of functioning as a tissue-selective VDR modulator.

The present specification encompasses the contents disclosed in the specification and/or drawings of Japanese Patent Application No. 2011-45022 based on which the present patent application claims priority.

BEST MODES FOR CARRYING OUT THE INVENTION

Figure 1:
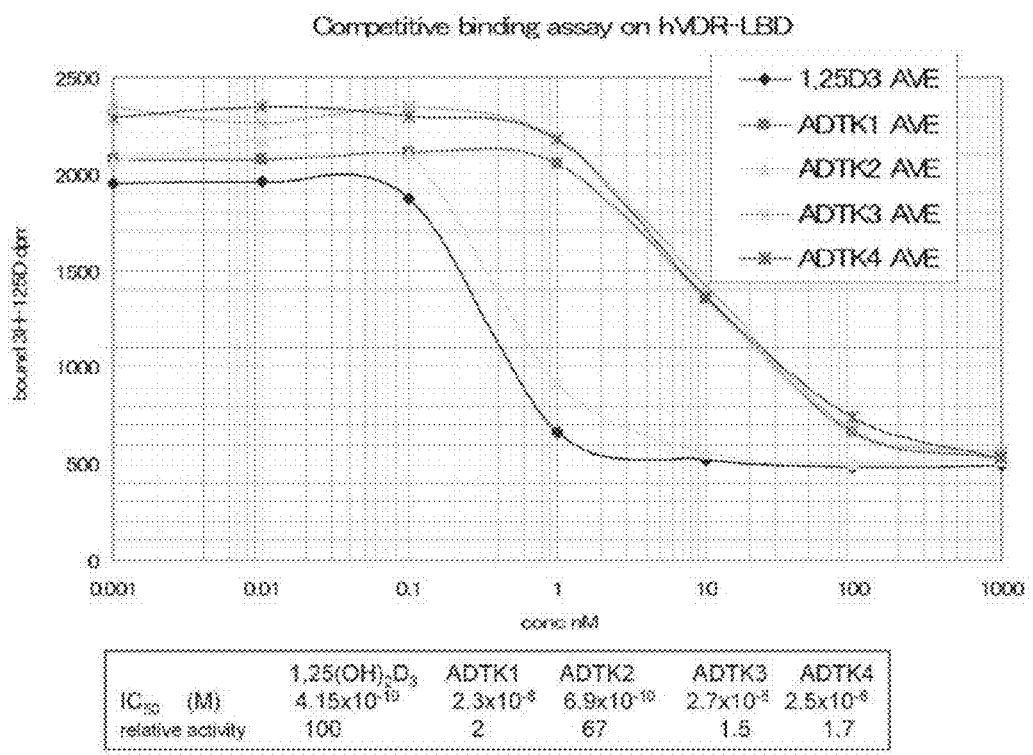
FIG. 1 shows the affinity of ADTK1 through ADTK4 for human VDR. In a competitive binding assay using human VDR and [$^3$H]-1,25(OH)$_2$D$_3$, ADTK2 exhibited an affinity (67%) almost comparable to that of the natural hormone 1,25(OH)$_2$D$_3$. Other compounds also exhibited a considerably strong affinity (about 1/50 of that of 1,25(OH)$_2$D$_3$).
ADTK1: (25S)-25-(1-Adamantyl)-1α,25-dihydroxy-2-methylene-23,23,24,24-tetradehydro-19,26,27-trinorvitamin $D_3$
ADTK2: (25R)-25-(1-Adamantyl)-1α,25-dihydroxy-2-methylene-23,23,24,24-tetradehydro-19,26,27-trinorvitamin $D_3$
ADTK3: (25R)-26-(1-Adamantyl)-1α,25-dihydroxy-2-methylene-23,23,24,24-tetradehydro-19,27-dinorvitamin $D_3$
ADTK4: (25S)-26-(1-Adamantyl)-1α,25-dihydroxy-2-methylene-23,23,24,24-tetradehydro-19,27-dinorvitamin $D_3$

Hereinbelow, the present invention will be described in detail.

The present invention provides a compound represented by the following formula (I), a solvate thereof or a prodrug thereof.

[Formula 2]

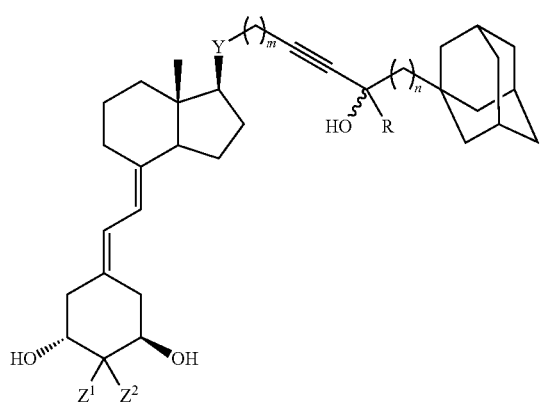

(I)

wherein m and n each independently represent 1 or 0;

R represents a hydrogen atom or an alkyl group;

Y represents an ethane-1,1-diyl group or an ethyne-1,2-diyl group; and $Z^1$ represents a hydrogen atom and $Z^2$ represents a hydroxyalkoxy group, or $Z^1$ and $Z^2$ jointly form a methylene group.

As the alkyl group represented by R, $C_{1-6}$ alkyl groups are suitable; $C_{1-3}$ alkyl groups are preferable; and $C_{1-2}$ alkyl groups are more preferable. Specific examples of the alkyl group include, but are not limited to, methyl, ethyl, n-propyl, isopropyl, n-butyl, isobutyl, sec-butyl, tert-butyl, n-pentyl, sec-pentyl, isopentyl, neopentyl, n-hexyl and isohexyl.

As the alkoxy group in the hydroxyalkoxy group represented by $Z^2$, $C_{1-6}$ alkoxy groups are suitable; $C_{1-3}$ alkoxy groups are preferable; and $C_3$ alkoxy groups are more preferable. Specific examples of the alkoxy group include, but are not limited to, methoxy, ethoxy, propoxy, n-butoxy, isobutoxy, sec-butoxy, tert-butoxy, n-pentoxy, sec-pentoxy, isopentoxy, neopentoxy, n-hexoxy and isohexoxy.

The compound represented by formula (I) may occur as stereoisomers. Both individual isomers and mixtures of isomers are encompassed by the present invention.

Specific examples of the compound represented by formula (I) include, but are not limited to, the following compounds.

(25S)-25-(1-Adamantyl)-1α,25-dihydroxy-2-methylene-23,23,24,24-tetradehydro-19,26,27-trinorvitamin $D_3$ (Hereinafter, sometimes referred to as "ADTK1").

(25R)-25-(1-Adamantyl)-1α,25-dihydroxy-2-methylene-23,23,24,24-tetradehydro-19,26,27-trinorvitamin $D_3$ (Hereinafter, sometimes referred to as "ADTK2").

(25R)-26-(1-Adamantyl)-1α,25-dihydroxy-2-methylene-23,23,24,24-tetradehydro-19,27-dinorvitamin $D_3$ (Hereinafter, sometimes referred to as "ADTK3").

(25S)-26-(1-Adamantyl)-1α,25-dihydroxy-2-methylene-23,23,24,24-tetradehydro-19,27-dinorvitamin $D_3$ (Hereinafter, sometimes referred to as "ADTK4").

(25R)-25-(1-Adamantyl)-1α,25-dihydroxy-2-methylene-20,20,22,22,23,23,24,24-octadehydro-19,21,26,27-tetranorvitamin $D_3$ (Hereinafter, sometimes referred to as "ADYW1").

(25S)-25-(1-Adamantyl)-1α,25-dihydroxy-2-methylene-20,20,22,22,23,23,24,24-octadehydro-19,21,26,27-tetranorvitamin $D_3$ (Hereinafter, sometimes referred to as "ADYW2").

(25R)-25-(1-Adamantyl)-1α,25-dihydroxy-2-methylene-23,23,24,24-tetradehydro-19,27-dinorvitamin $D_3$ (Hereinafter, sometimes referred to as "ADKM1").

(25S)-25-(1-Adamantyl)-1α,25-dihydroxy-2-methylene-23,23,24,24-tetradehydro-19,27-dinorvitamin $D_3$ (Hereinafter, sometimes referred to as "ADKM2").

[Formula 3]

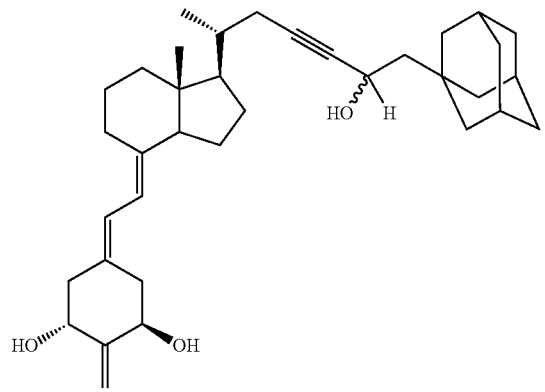

ADTK1 (25S)
ADTK2 (25R)

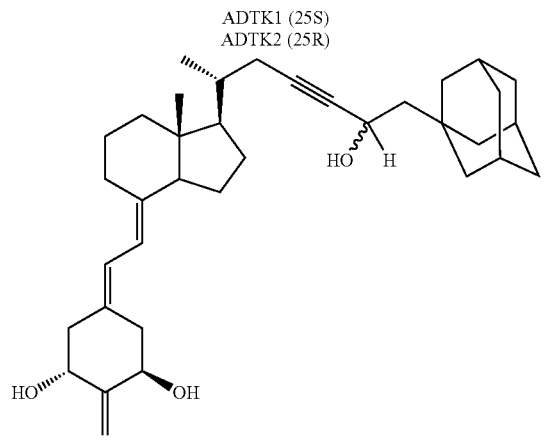

ADTK3 (25R)
ADTK4 (25S)

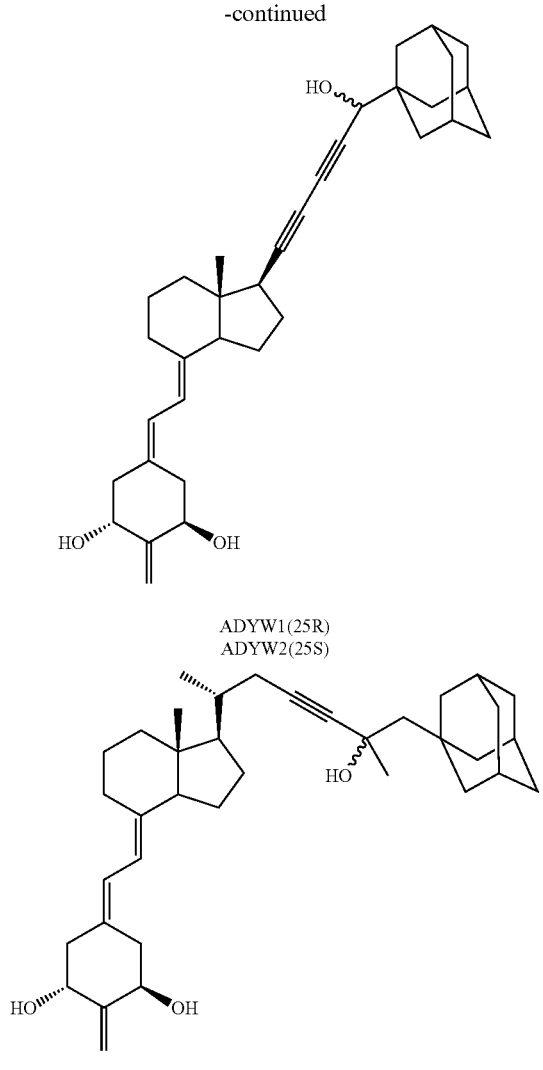

ADYW1(25R)
ADYW2(25S)

ADKM1 (25R)
ADKM2 (25S)

The compound represented by formula (I) wherein R is a hydrogen atom; Y is an ethane-1,1-diyl group; m is 1; n is 0 or 1; and $Z^2$ and $Z^2$ jointly form a methylene group may be prepared by the method disclosed in Example 1 described later or the method with necessary modifications.

The compound represented by formula (I) wherein R is a hydrogen atom (or an alkyl group); Y is an ethane-1,1-diyl group; m is 0; n is 0 or 1; and $Z^2$ and $Z^2$ jointly form a methylene group may be synthesized according to scheme 2 provided below. Briefly, 22-tosylate form 1 is oxidized into an aldehyde form 7 which is then subjected to Seyferth-Gilbert homologation to synthesize an acetylene form 8. Subsequently, the resultant product is reacted with adamantyl aldehyde (n=0 or 1) in the same manner as in the synthesis of ADTK compounds to thereby obtain a propargyl alcohol form (9 or 10). After removal of the protective group, the adamantyl vitamin D derivative of interest can be obtained. When R is an alkyl group, compounds 9 and 10 are oxidized into ketone forms, which are then alkylated to obtain the compound of interest (in the same manner as in the synthesis of ADKM1 and ADKM2; see Example 5 described later).

Scheme 2

[Formula 4]

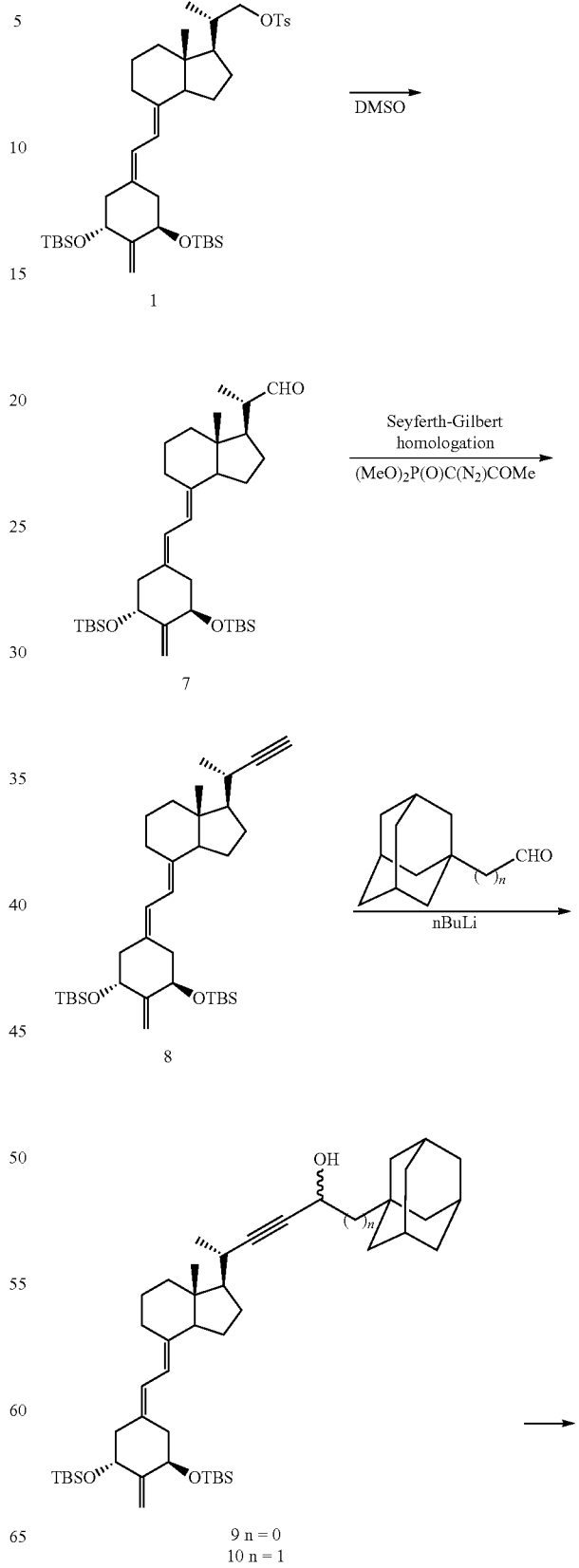

9 n = 0
10 n = 1

-continued

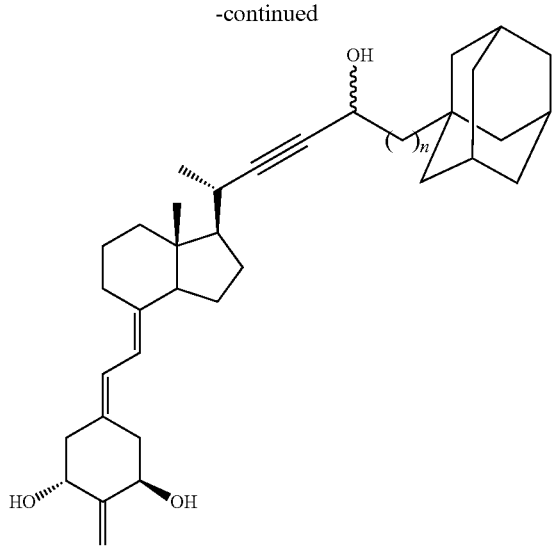

n = 0 or 1

The compound represented by formula (I) wherein R is an alkyl group; Y is an ethane-1,1-diyl group; m is 1; n is 0 or 1; and $Z^2$ and $Z^2$ jointly form a methylene group may be synthesized according to scheme 3 provided below. Briefly, the alcohol at position 25 of compound 3 or 4 shown in the scheme disclosed in Example 1 described later is oxidized to form a ketone form (11), which is then reacted with an alkyl metal reagent (eg., MeMgBr, EtMgBr, MeLi or BuLi) to prepare 25-alkyl form (12). After removal of the protective group, the compound of interest can be obtained (see Example 5 described later). Alternatively, the compound of interest may be obtained by treating a carbamoylated form (13: Cb: i-Pr$_2$NCO) of 25-hydroxyl group of compound 3 or 4 with a strong base and then treating the resultant compound with a boronic acid derivative or alkylborane to thereby introduce an alkyl group (14). After removal of the protective group, the compound of interest can be obtained.

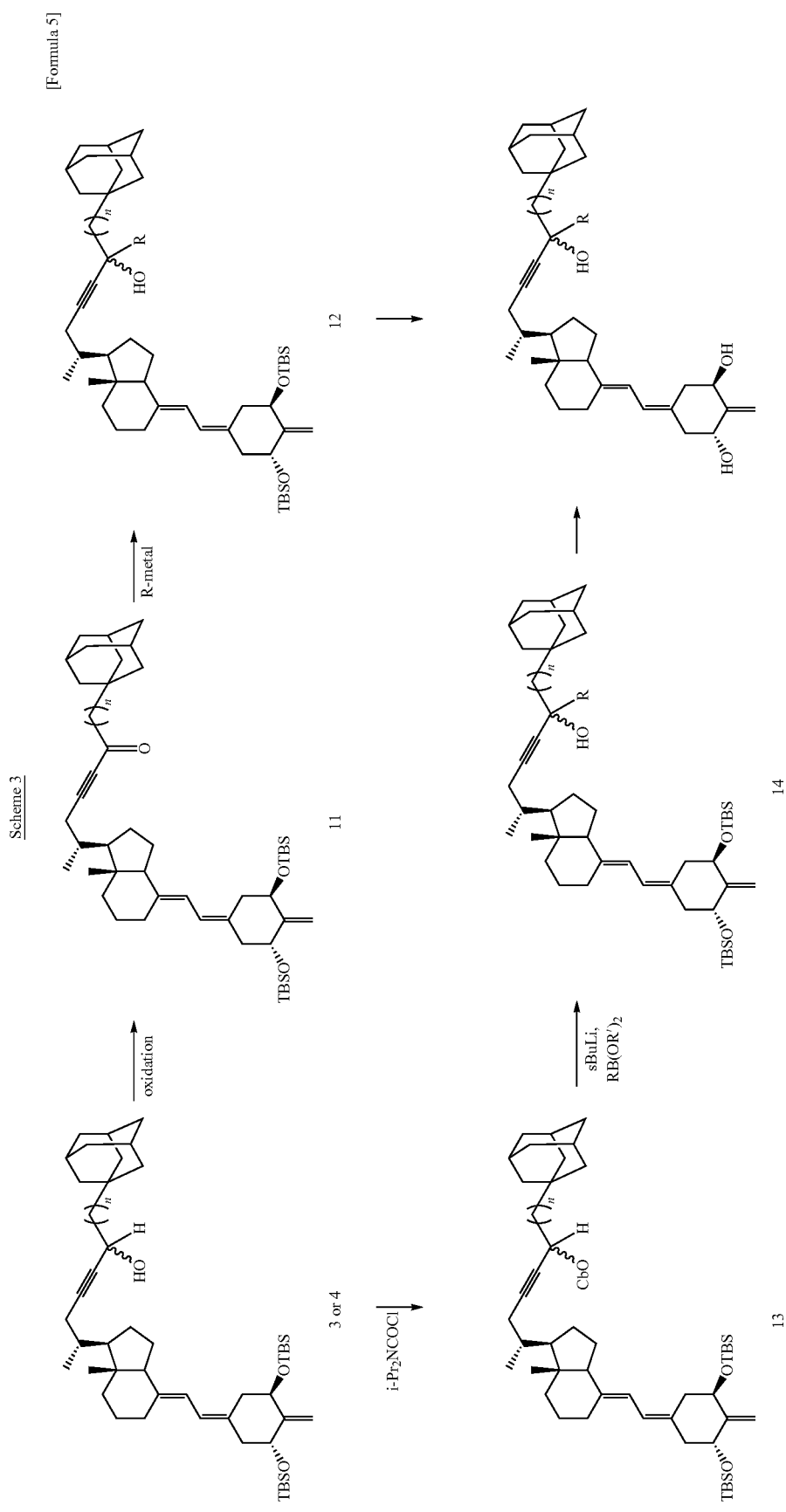

The compound represented by formula (I) wherein R is a hydrogen atom; Y is an ethyne-1,2-diyl group; m is 0; n is 0; and $Z^2$ and $Z^2$ jointly form a methylene group may be synthesized by the method disclosed in Example 4 described later or the method with necessary modifications.

The compound represented by formula (I) wherein R is a hydrogen atom; Y is an ethyne-1,2-diyl group; m is 0; n is 1; and $Z^1$ and $Z^2$ jointly form a methylene group may be synthesized by the scheme shown below or the scheme with necessary modifications.

[Formula 6]

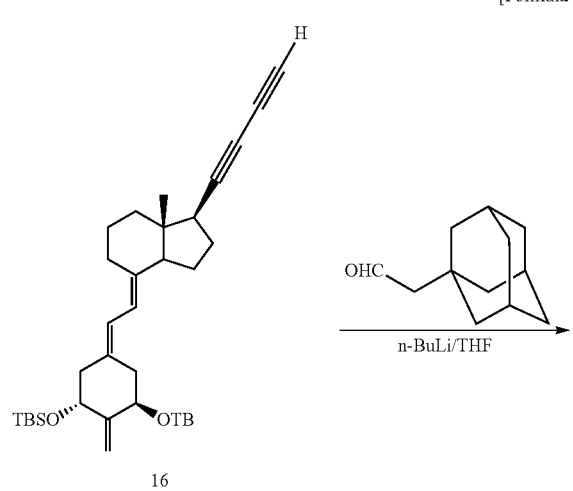

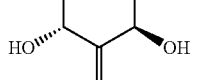

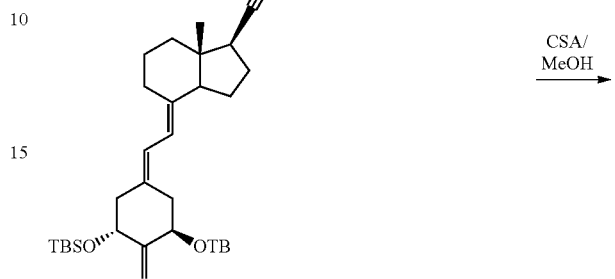

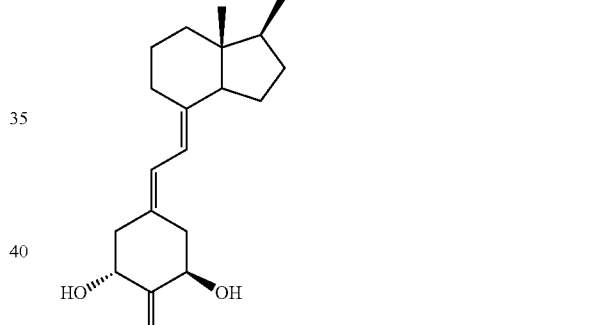

ADYW3: 25R
ADYW4: 25S

The compound represented by formula (I) wherein R is an alkyl group; Y is an ethyne-1,2-diyl group; m is 0; n is 0 or 1; and $Z^1$ and $Z^2$ jointly form a methylene group may be synthesized by the scheme shown below or the scheme with necessary modifications.

[Formula 7]
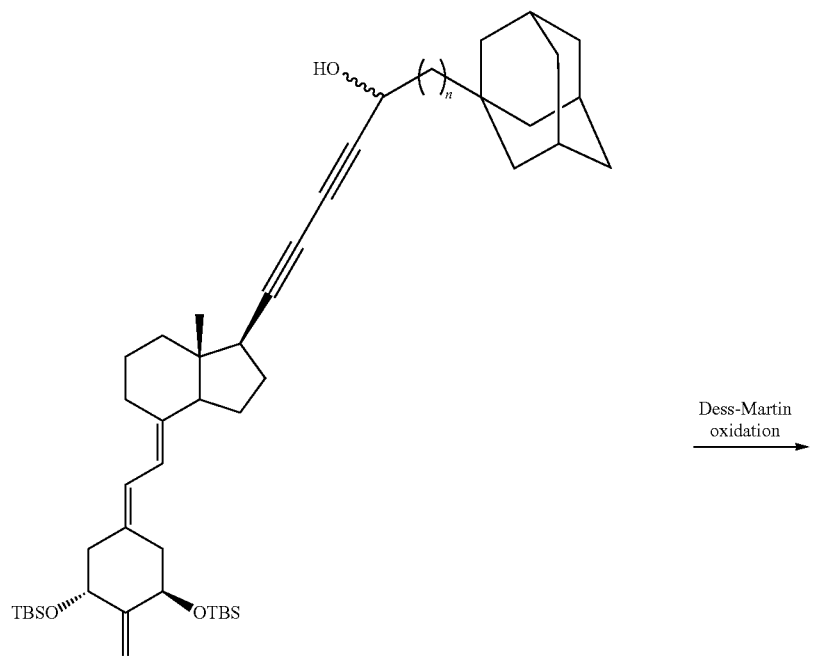
17
Dess-Martin oxidation →
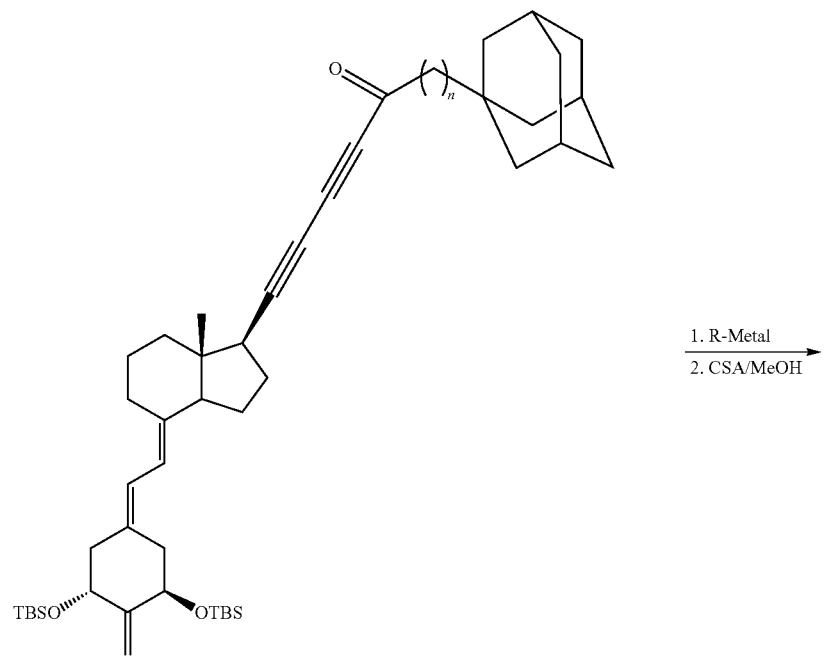
20
1. R-Metal
2. CSA/MeOH
→

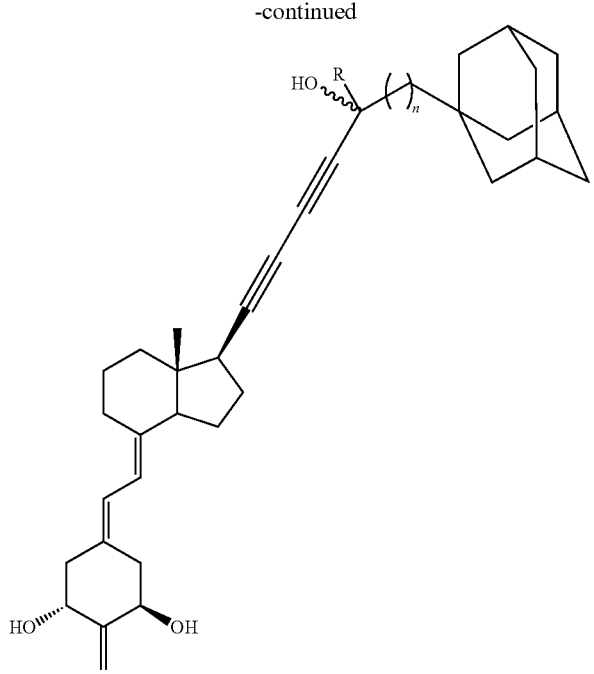
21
The compound represented by formula (I) wherein $Z^1$ is a hydrogen atom; and $Z^2$ is a hydroxyalkoxy group may be synthesized by the scheme shown below or the scheme with necessary modifications.
[Formula 8]
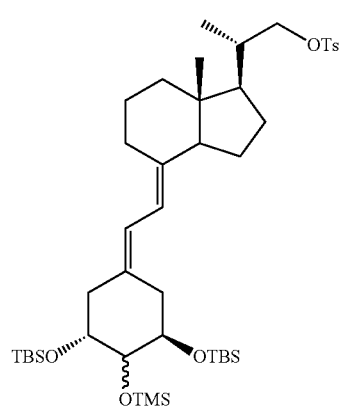
ref. Igarashi M. et al.,
Arch Biochem. Biophys.
2007, 460, 240-53.
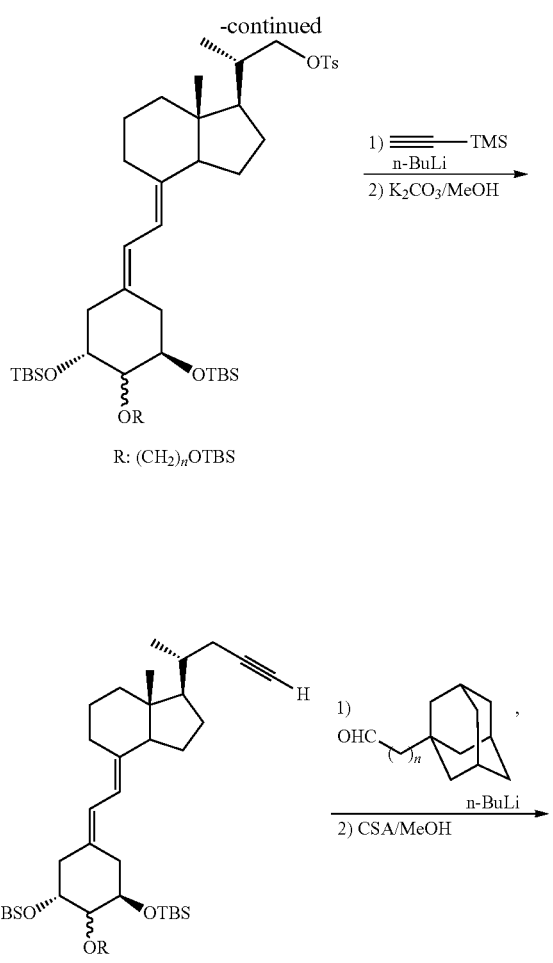

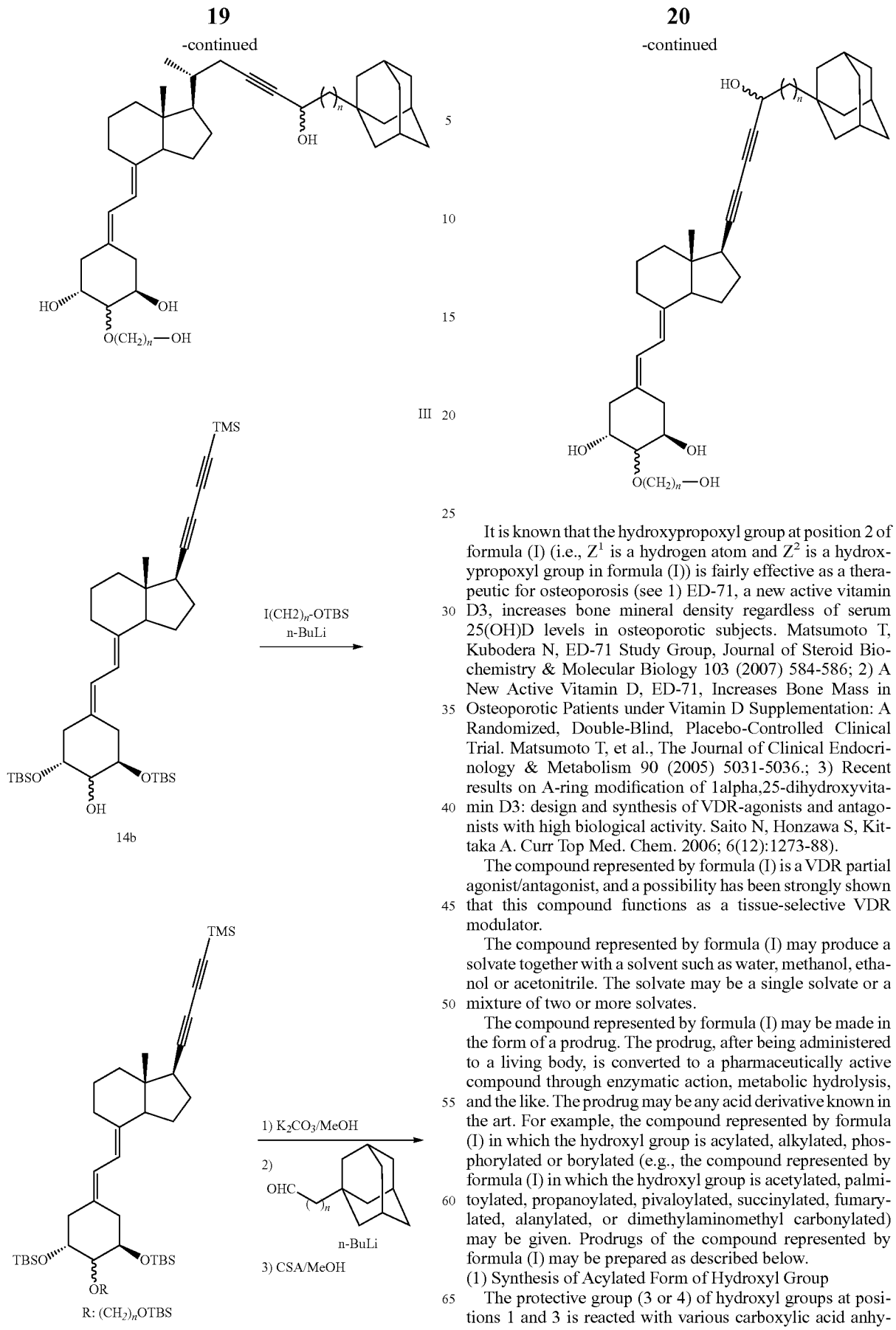

It is known that the hydroxypropoxyl group at position 2 of formula (I) (i.e., $Z^1$ is a hydrogen atom and $Z^2$ is a hydroxypropoxyl group in formula (I)) is fairly effective as a therapeutic for osteoporosis (see 1) ED-71, a new active vitamin D3, increases bone mineral density regardless of serum 25(OH)D levels in osteoporotic subjects. Matsumoto T, Kubodera N, ED-71 Study Group, Journal of Steroid Biochemistry & Molecular Biology 103 (2007) 584-586; 2) A New Active Vitamin D, ED-71, Increases Bone Mass in Osteoporotic Patients under Vitamin D Supplementation: A Randomized, Double-Blind, Placebo-Controlled Clinical Trial. Matsumoto T, et al., The Journal of Clinical Endocrinology & Metabolism 90 (2005) 5031-5036.; 3) Recent results on A-ring modification of 1alpha,25-dihydroxyvitamin D3: design and synthesis of VDR-agonists and antagonists with high biological activity. Saito N, Honzawa S, Kittaka A. Curr Top Med. Chem. 2006; 6(12):1273-88).

The compound represented by formula (I) is a VDR partial agonist/antagonist, and a possibility has been strongly shown that this compound functions as a tissue-selective VDR modulator.

The compound represented by formula (I) may produce a solvate together with a solvent such as water, methanol, ethanol or acetonitrile. The solvate may be a single solvate or a mixture of two or more solvates.

The compound represented by formula (I) may be made in the form of a prodrug. The prodrug, after being administered to a living body, is converted to a pharmaceutically active compound through enzymatic action, metabolic hydrolysis, and the like. The prodrug may be any acid derivative known in the art. For example, the compound represented by formula (I) in which the hydroxyl group is acylated, alkylated, phosphorylated or borylated (e.g., the compound represented by formula (I) in which the hydroxyl group is acetylated, palmitoylated, propanoylated, pivaloylated, succinylated, fumarylated, alanylated, or dimethylaminomethyl carbonylated) may be given. Prodrugs of the compound represented by formula (I) may be prepared as described below.

(1) Synthesis of Acylated Form of Hydroxyl Group

The protective group (3 or 4) of hydroxyl groups at positions 1 and 3 is reacted with various carboxylic acid anhydrides or halides in the presence of a weak base (pyridine, triethylamine or the like). After deprotection of positions 1 and 3, an acylated form of 25-hydroxyl group can be obtained.

The final vitamin D derivative is acylated in the same manner to prepare 1,3,25-triacylated form, which is then acylated under milder conditions to yield 1,3-diacylated form.

(2) Synthesis of Alkyl Ether of Hydroxyl Group

The protective group (3 or 4) of hydroxyl groups at positions 1 and 3 is treated with a strong base (n-BuLi, NaH or the like) and then reacted with an alkyl halide to synthesize an alkyl ether form of 25-hydroxyl group. After deprotection of positions 1 and 3, the alkyl ether of interest can be obtained.

The final vitamin D derivative is alkylated in the same manner to prepare 1,3,25-trialkyl ether form, which is then alkylated under milder conditions to yield 1,3-dialkyl ether form.

Further, the present invention provides a composition comprising a compound represented by formula (I), a solvate thereof or a prodrug thereof.

The compound represented by formula (I), solvate thereof or prodrug thereof may be used for activating VDRs, especially as a tissue-selective VDR modulator. This drug can be used as a pharmaceutical or a reagent for experiments.

When used as a pharmaceutical, the compound, solvate or prodrug can be used in the prevention and/or treatment of diseases in which a vitamin D receptor is involved. More specifically, the drug can be used in the prevention and/or treatment of osteoporosis, malignant neoplasms (e.g., myeloid leukemia, breast cancer, prostate cancer, colon cancer, etc.), psoriasis vulgaris, autoimmune diseases (e.g., chronic rheumatoid arthritis, systemic lupus erythematosus, etc.), infectious diseases (e.g., tuberculosis, etc.), neurodegenerative diseases (e.g., multiple sclerosis, etc.), disorders in glucose/lipid metabolism (e.g., diabetes mellitus, etc.), cardiovascular diseases (e.g., hypertension), and the like.

When used as a pharmaceutical, a compound represented by formula (I), a solvate thereof or a prodrug thereof may be used alone, or may be mixed with excipients or carriers to formulate tablets, capsules, powders, granules, solutions or suspensions, syrups, aerosols, suppositories, injections, or the like. The excipient or carrier may be those which are routinely used in the art and are pharmaceutically acceptable, and the type and composition thereof may be varied appropriately. For example, water or a vegetable oil is used as a liquid carrier. Solid carriers that may be used include saccharides such as lactose, saccharose and glucose; starches such as potato starch and corn starch; cellulose derivatives such as microcrystalline cellulose, etc. A lubricant such as magnesium stearate, a binder such as gelatin or hydroxypropyl cellulose, a disintegrant such as carboxymethyl cellulose, and the like may also be added. In addition, an antioxidant, a colorant, a flavor, a preservative, and the like may further be added. The drug may also be used in the form of a lyophilized formulation.

A compound represented by formula (I), a solvate thereof or a prodrug thereof may be administered via various routes such as oral, transnasal, rectal, transdermal, subcutaneous, intravenous or intramuscular route.

The content of a compound represented by formula (I), a solvate thereof or a prodrug thereof in pharmaceutical preparations varies depending on the type of the preparation, but the content is usually 1 to 100% by weight, preferably 50 to 100% by weight. For example, the content of the compound, solvate or prodrug in solutions or suspensions is preferably 1 to 100% by weight in the pharmaceutical preparation. For capsules, tablets, granules and powders, the content of the compound, solvate or prodrug is usually about 10 to about 100% by weight, preferably 50 to 100% by weight, in the pharmaceutical preparation, with the remainder being a carrier. The pharmaceutical may be prepared in unit dose formulations.

The dose of a compound represented by formula (I), a solvate thereof or a prodrug thereof may be any amount that allows the expected preventive and/or therapeutic effects to be confirmed. The dose varies depending on the dosage form, administration route, the age and weight of the patient, the type and severity of the disease. For example, the dose is about 5-50 μg/kg body weight per administration for an adult as calculated for the active ingredient. This dose may be administered once to several times per day.

Hereinbelow, the present invention will be described more specifically with reference to the following Examples. However, the scope of the present invention is not limited by these Examples.

EXAMPLES

Example 1

Synthesis of ADTK1 through ADTK4

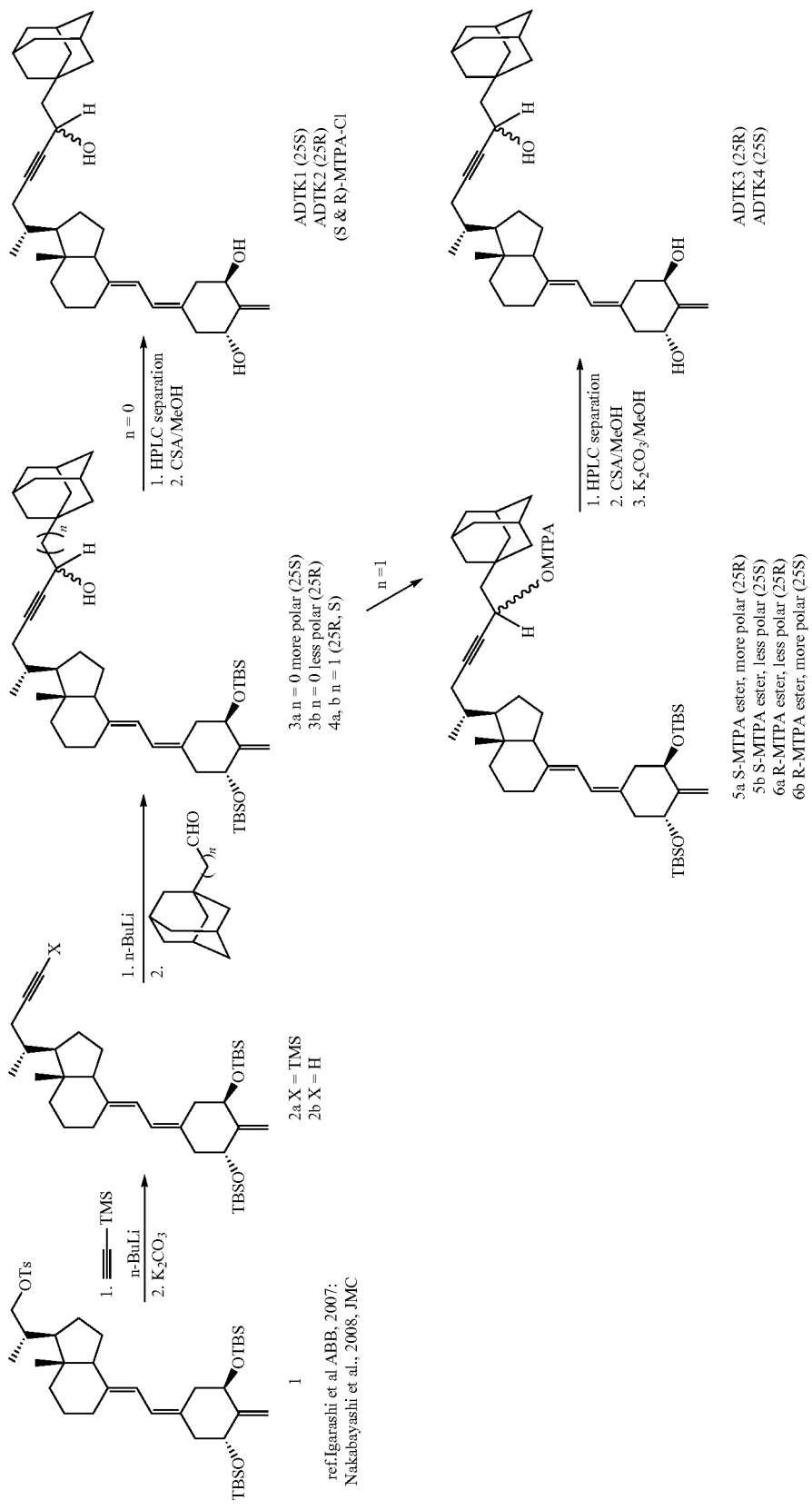

(1) Synthesis of 1α-Hydroxy-2-methylene-24-trimethylsilyl-23,23,24,24-tetradehydro-19,25,26,27-tetranorvitamin D$_3$ 1,3-bis-(tert-butyldimethylsilyl)ether (2a)

A solution of trimethylsilylacetylene (76.0 μL, 0.55 mmol, 6 eq) in anhydrous dioxane (850 μL) was cooled to 0° C. To this solution was added n-butyllithium (1.6 M in hexane, 211 μL, 0.55 mmol, 6 eq). The mixture was stirred at 0° C. for 30 min and then at room temperature for 30 min. To the resultant solution, a solution of tosyl form 1 (67.2 mg, 0.092 mmol) in anhydrous dioxane (2.8 mL) was added slowly. The reaction solution was stirred at 120° C. for 20 hr in a sealed tube. Saturated brine was added to the reaction mixture, which was then extracted with ethyl acetate. The organic layer was washed with saturated brine, dried over anhydrous magnesium sulfate and evaporated. The residue was purified by column chromatography (SiO$_2$, 4.0 g) to obtain 2a (26.5 mg, 61.9%) from 0.5% ethyl acetate/hexane elution part.

2a: $^1$H NMR (CDCl$_3$, δ) 0.02, 0.05, 0.055, 0.06 (each 3H, s), 0.155 (9H, s), 0.86, 0.90 (each 9H, s), 1.09 (3H, d, J=6.4 Hz), 2.03-2.08 (1H, m), 2.18 (1H, dd, J=14, 8 Hz), 2.29-2.34 (2H, m), 2.44-2.53 (2H, m), 2.82 (1H, dd, J=12, 3.2 Hz), 4.41-4.45 (2H, m), 4.92 (1H, s), 4.97 (1H, s), 5.84 (1H, d, J=11.2 Hz), 6.21 (1H, d, J=11.2 Hz).

MS m/z (%): 654 (M$^+$, 2), 522 (30), 450 (10), 366 (10), 234 (10), 73 (100).

(2) Synthesis of 1α-Hydroxy-2-methylene-23,23,24,24-tetradehydro-19,25,26,27-tetranorvitamin D$_3$ 1,3-bis-(tert-butyldimethylsilyl)ether (2b)

To a solution of TMS acetylene form 2a (27.0 mg, 0.041 mmol) in THF/methanol (1:0.7, 850 μL), potassium carbonate (28.5 mg, 0.21 mmol, 5 eq) was added. The mixture was stirred at room temperature for 24 hr. Saturated ammonium chloride solution was added to the reaction mixture at 0° C., followed by extraction with ethyl acetate. The organic layer was washed with saturated brine, dried over anhydrous magnesium sulfate and evaporated. The residue was purified by column chromatography (SiO$_2$, 6.8 g) to obtain 2b (22.8 mg, 95%) from 1% ethyl acetate/hexane elution part.

2b: $^1$H NMR (CDCl$_3$, δ) 0.02, 0.05, 0.06, 0.07 (each 3H, s), 0.86, 0.90 (each 9H, s), 1.09 (3H, d, J=6.4 Hz), 1.95 (1H, t, J=2.4 Hz), 2.01-2.08 (1H, m), 2.18 (1H, dd, J=14, 8 Hz), 2.27 (1H, dt, J=17, 2.8 Hz), 2.32 (1H, dd, J=13.4, 3.2 Hz), 2.44-2.53 (2H, m), 2.82 (1H, dd, J=12, 3.2 Hz), 4.41-4.45 (2H, m), 4.92 (1H, s), 4.97 (1H, s), 5.84 (1H, d, J=11.2 Hz), 6.21 (1H, d, J=11.2 Hz).

MS m/z (%): 582 (M$^+$, 2), 450 (65), 366 (18), 351 (10), 234 (18), 73 (100).

(3) Synthesis of 25-(1-Adamantyl)-1α,25-dihydroxy-2-methylene-23,23,24,24-tetradehydro-19,26,27-trinorvitamin D$_3$ 1,3-bis-(tert-butyldimethylsilyl)ether (3)

To a solution of acetylene form 2b (6.1 mg, 0.010 mmol) in THF (200 μL), a solution of n-butyllithium in hexane (19.2 μL, 1.6 M, 0.050 mmol, 5 eq) was added in argon at 0° C. under stirring. After stirring for 10 min, a solution of 1-formyladamantane (4.92 mg, 0.030 mmol, 3 eq) in THF (70 μL) was added slowly to the reaction mixture, followed by stirring at 0° C. for 1 hr. Saturated ammonium chloride was added to the reaction solution at 0° C., followed by extraction with ethyl acetate. The organic layer was washed with saturated sodium chloride solution, dried over anhydrous magnesium sulfate and evaporated. The residue was purified by silica gel column chromatography (1.2 g) to obtain alcohol form 3 (4.7 mg, 63.0%) as a 1:1 mixture of 25-epimers from 1% ethyl acetate/hexane elution part. This mixture was separated by normal phase HPLC [Hibar RT LiChrosorb Si 60 (7 μm) 10 mm×250 mm; CH$_2$Cl$_2$/hexane, 2/3, 4.0 mL/min] to obtain a less polar (25R) form (3b) and a more polar (25S) form (3a).

3: $^1$HNMR (CDCl$_3$, δ) 0.02, 0.05, 0.07, 0.08 (each 3H, s), 0.56 (3H, s), 0.86, 0.90 (each 9H, s), 1.06-1.12 (3H, m), 2.15-2.20 (1H, m), 2.29-2.38 (3H, m), 2.45-2.54 (2H, m), 3.89 (1H, s), 4.41-4.45 (2H, m), 4.92 (1H, s), 4.97 (1H, s), 5.84 (1H, d, J=11.2 Hz), 6.21 (1H, d, J=11.2 Hz).

MS m/z (%): 746 (M$^+$, 2), 614 (18), 596 (20), 366 (20), 234 (12), 135 (100), 73 (80).

(4) Synthesis of (25S)-25-(1-Adamantyl)-1α,25-dihydroxy-2-methylene-23,23,24,24-tetradehydro-19,26,27-trinorvitamin D$_3$ (ADTK1)

A methanol solution of TBS ether 3a (more polar; 1.07 mg, 0.0014 mmol) (500 μL) was cooled to 0° C. To this solution was added a methanol solution of (±)-10-camphorsulfonic acid (1.31 mg, 0.0056 mmol, 4 eq) (300 μL). The mixture was stirred at room temperature for 2 hr. Saturated sodium hydrogencarbonate solution was added to the reaction mixture at 0° C., followed by extraction with ethyl acetate. The organic layer was washed with saturated brine, dried over anhydrous magnesium sulfate and evaporated. The residue was purified by silica gel column chromatography (1.5 g) to obtain ADTK 1 (331 μg, 45.6%) from 40% ethyl acetate/hexane elution part.

ADTK 1: $^1$H NMR (CDCl3 δ) 0.57 (3H, s), 1.10 (3H, d, J=8.0 Hz), 2.12-2.19 (1H, m), 2.25-2.36 (2H, m), 2.58 (1H, dd, J=12, 4 Hz), 2.80-2.87 (2H, m), 3.86 (1H, d, J=4 Hz), 4.46-4.50 (2H, m), 5.10 (1H, s), 5.11 (1H, s), 5.89 (1H, d, J=12 Hz), 6.36 (1H, d, J=12 Hz).

$^{13}$C NMR (CDCl$_3$ δ) 12.2, 19.4, 22.2, 22.7, 23.4, 26.0, 27.5, 28.3, 28.9, 29.7, 35.7, 37.5, 38.1, 40.3, 45.7, 45.8, 55.3, 56.3, 70.7, 71.8, 71.9, 80.3, 85.1, 107.8, 115.4, 124.2, 130.6, 143.1, 151.9.

MS m/z (%): 518 (M$^+$, 10), 365 (10), 347 (10), 295 (10), 135 (100), 93 (25), 79 (25).

(5) Synthesis of (25R)-25-(1-Adamantyl)-1α,25-dihydroxy-2-methylene-23,23,24,24-tetradehydro-19,26,27-trinorvitamin D$_3$ (ADTK2)

TBS ether 3b (less polar; 1.35 mg, 0.0018 mmol) was treated with CSA (1.68 mg, 0.0072 mmol, 4 eq) in the same manner as described above for ether 3a. The reaction product was purified by silica gel column chromatography (1.0 g) to obtain ADTK 2 (416 μg, 44.0%) from 50% ethyl acetate/hexane elution part.

ADTK 2: $^1$H NMR (CDCl$_3$, δ) 0.57 (3H, s), 1.10 (3H, d, J=8.0 Hz), 2.12-2.19 (1H, m), 2.25-2.36 (2H, m), 2.58 (1H, dd, J=12, 4 Hz), 2.80-2.87 (2H, m), 3.86 (1H, d, J=4 Hz), 4.46-4.50 (2H, m), 5.10 (1H, s), 5.11 (1H, s), 5.89 (1H, d, J=12 Hz), 6.36 (1H, d, J=12 Hz).

$^{13}$C NMR (CDCl$_3$ δ): 12.2, 19.4, 22.2, 22.7, 23.4, 26.0, 27.5, 28.3, 28.9, 29.7, 35.7, 37.5, 38.1, 40.3, 45.7, 45.8, 55.3, 56.3, 70.7, 71.8, 71.9, 80.3, 85.1, 107.8, 115.4, 124.2, 130.6, 143.1, 151.9.

MS m/z (%): 518 (M$^+$, 10), 365 (10), 347 (10), 295 (10), 135 (100), 93 (25), 79 (25).

(6) Synthesis of 26-(1-Adamantyl)-1α,25-dihydroxy-2-methylene-23,23,24,24-tetradehydro-19,27-dinorvitamin $D_3$ 1,3-bis-(tert-butyldimethylsilyl) ether (4)

To a solution of acetylene form 2b (6.4 mg, 0.011 mmol) in anhydrous THF (150 μL), a hexane solution of n-butyllithium (21.1 μL, 1.6 M, 0.055 mmol, 5 eq) was added under argon gas flow at 0° C. The mixture was left for 10 min. Subsequently, a solution of 2-(1-adamantyl)acetaldehyde (5.88 mg, 0.033 mmol, 3 eq) in anhydrous THF (60 μL) was added to the mixture and stirred at 0° C. for 1 hr. Saturated ammonium chloride solution was added to the reaction solution at 0° C., followed by extraction with ethyl acetate. The organic layer was washed with saturated sodium chloride, dried over anhydrous magnesium sulfate and evaporated. The residue was purified by column chromatography ($SiO_2$, 1.1 g) to obtain alcohol form 4 (5.3 mg, 80.4%) as an approx. 1:1 mixture of 25-epimers from 1% ethyl acetate/hexane elution part.

4: $^1$H NMR ($CDCl_3$ δ) 0.02, 0.05, 0.06, 0.08 (each 3H, s), 0.55 (3H, s), 0.86, 0.90 (each 9H, s), 1.06 (3H, d, J=8.0 Hz), 2.13-2.20 (1H, m), 2.25-2.34 (2H, m), 2.44-2.54 (2H, m), 4.41-4.45 (2H, m), 4.50 (1H, t, J=6.4 Hz), 4.92 (1H, s), 4.97 (1H, s), 5.84 (1H, d, J=11.2 Hz), 6.21 (1H, d, J=11.2 Hz).

MS m/z (%): 760 ($M^+$, 2), 610 (16), 475 (18), 366 (20), 234 (12), 135 (100), 73 (75).

(7) Synthesis of 25-[(S)-α-Methoxy-α-(triflouoromethyl)phenylacetyl]ester of 26-(1-adamantyl)-1α,25-dihydroxy-2-methylene-23,23,24,24-tetradehydro-19,27-dinorvitamin $D_3$ 1,3-bis-(tert-butyldimethylsilyl)ether (5)

A solution of propargyl alcohol form 4 (5.2 mg, 0.0068 mmol) in anhydrous dichloromethane (600 μL) was cooled to 0° C. Triethylamine (9.46 μL, 0.068 mmol, 10 eq) and 4-dimethylaminopyridine (4.63 mg, 0.038 mmol, 5.6 eq) were added thereto. Subsequently, a solution of (S)-(+)-α-(trifluoromethyl)phenylacetylchloride (MTPA-Cl 4.63 mg, 0.038 mmol, 5.6 eq) in anhydrous dichloromethane (450) was added thereto. The resultant mixture was stirred at 0° C. for 5 min and at room temperature for 30 min. Ice water was added to the reaction mixture, followed by extraction with ethyl acetate/hexane (1:1). The organic layer was washed with saturated brine, dried over anhydrous magnesium sulfate and evaporated. The residue was purified by column chromatography ($SiO_2$, 5.0 g) to obtain MTPA ester 5 (5.4 mg, 80.9%) as an approx. 1:1 mixture of 25-epimers from 2% ethyl acetate/hexane elution part. This mixture was separated by normal phase HPLC [Hibar RT LiChrosorb Si 60 (7 μm); 10 mm×250 mm; $CH_2Cl_2$/hexane 2/3, 4.0 mL/min] to obtain a less polar (25S)-ester 5b and a more polar (25R)-ester 5a.

5a: $^1$H NMR ($CDCl_3$ δ) 0.02, 0.05, 0.06, 0.08 (each 3H, s), 0.54 (3H, s), 0.86, 0.90 (each 9H, s), 1.04 (3H, d, J=6.4 Hz), 1.55-1.58 (2H, m), 2.02-2.08 (1H, m), 2.18 (1H, dd, J=14, 8 Hz), 2.20-2.26 (1H, m), 2.44-2.54 (2H, m), 3.53 (3H, s), 4.41-4.45 (2H, m), 4.92 (1H, s), 4.97 (1H, s), 5.60 (1H, t, J=6.4 Hz), 5.83 (1H, d, J=11.2 Hz), 6.21 (1H, d, J=11.2 Hz), 7.37-7.56 (5H, m).

5b: $^1$H NMR ($CDCl_3$ δ) 0.02, 0.05, 0.06, 0.08 (each 3H, s), 0.54 (3H, s), 0.86, 0.90 (each 9H, s), 1.03 (3H, d, J=6.4 Hz), 1.54-1.56 (2H, m), 2.08 (1H, ddd, J=17, 8, 2 Hz), 2.18 (1H, dd, J=14, 8 Hz), 2.23-2.34 (2H, m), 2.44-2.54 (2H, m), 3.53 (3H, s), 4.41-4.45 (2H, m), 4.92 (1H, s), 4.97 (1H, s), 5.60 (1H, t, J=6.4 Hz), 5.83 (1H, d, J=11.2 Hz), 6.21 (1H, d, J=11.2 Hz), 7.37-7.56 (5H, m).

(8) Synthesis of (25R)-26-(1-Adamantyl)-1α,25-dihydroxy-2-methylene-23,23,24,24-tetradehydro-19,27-dinorvitamin $D_3$ (ADTK3)

A methanol solution of ester 5a (more polar; 1.03 mg, 0.0010 mmol) (500 μL) was cooled to 0° C. A methanol solution of (±)-(10)-camphorsulfonic acid (CSA, 1.22 mg, 0.0052 mmol, 5 eq) (200 μL) was added thereto, followed by stirring at room temperature for 3 hr. Saturated sodium hydrogencarbonate solution was added to the reaction mixture at 0° C., followed by extraction with ethyl acetate. The organic layer was washed with saturated brine, dried over anhydrous magnesium sulfate and evaporated. To a methanol solution of the residue (600 μL), potassium carbonate (130 mg) was added, followed by stirring at room temperature for 24 hr. Saturated ammonium chloride solution was added to the reaction mixture at 0° C., followed by extraction with ethyl acetate. The organic layer was washed with saturated brine, dried over anhydrous magnesium sulfate and evaporated. The residue was purified by column chromatography (Sephadex LH-20, 1.0 g) to obtain ADTK 3 (161 μg, 43.0%) from chloroform/hexane/methanol (70/30/1) elution part.

ADTK 3: $^1$H NMR ($CDCl_3$ δ) 0.56 (3H, s), 1.07 (3H, d, J=6.4 Hz), 1.95-2.11 (1H, m), 2.33-2.36 (3H, m), 2.57-2.59 (1H, m), 2.81-2.86 (2H, m), 4.48-4.51 (3H, m), 5.10 (1H, s), 5.11 (1H, s), 5.88 (1H, d, J=11.2 Hz), 6.36 (1H, d, J=11.2 Hz).

MS m/z (%): 532 ($M^+$, 10), 429 (10), 361 (10), 309 (10), 135 (100), 93 (40), 79 (40).

(9) Synthesis of (25S)-26-(1-Adamantyl)-1α,25-dihydroxy-2-methylene-23,23,24,24-tetradehydro-19,27-dinorvitamin $D_3$ (ADTK4)

(S)-MTPA ester 5b (less polar; 1.05 mg, 0.0011 mmol) was treated with CSA/MeOH to remove TBS group in the same manner as described above for ester 5a, and then treated with $K_2CO_3$/MeOH to remove MTPA group. The resultant product was purified by Sephadex LH-20 column chromatography (3.0 g, $CHCl_3$/hexane/MeOH 70/30/1) to obtain ADTK 4 (285 μg, 45.4%).

ADTK 4: $^1$H NMR ($CDCl_3$, δ) 0.56 (3H, s), 1.07 (3H, d, J=6.4 Hz), 2.00-2.10 (1H, m), 2.26-2.36 (3H, m), 2.56-2.59 (1H, m), 2.81-2.87 (2H, m), 4.46-4.52 (3H, m), 5.10 (1H, s), 5.11 (1H, s), 5.88 (1H, d, J=11.2 Hz), 6.36 (1H, d, J=11.2 Hz).

MS m/z (%): 532 ($M^+$, 10), 429 (10), 361 (10), 309 (10), 135 (100), 93 (40), 79 (40).

Example 2

The binding of compounds ADTK1 through ADTK4 to human VDR was evaluated according to the method described in literature (Ishizawa et al., J Lipid Res 49:763, 2008).

The results are shown in FIG. 1. In the competitive binding assay using human VDR and [$^3$H]-1,25(OH)$_2D_3$, ADTK2 exhibited an almost comparable affinity (67%) to the natural hormone 1,25(OH)$_2D_3$. Other compounds also exhibited considerably strong binding activities that were around 1/50 of the activity of 1,25(OH)$_2D_3$.

Example 3

According to the methods described in literature (Ishizawa et al., J Lipid Res 49: 763, 2008; Igarashi et al., Arch Biochem Biophys 460: 240, 2007), the VDR transcription induction activity of compounds ADTK1 through ADTK4 was evaluated using human embryonic kidney (HEK) 293 cells by a luciferase (Luc) assay with a Luc reporter having mouse osteopontin vitamin D response element (VDRE) (SPP) in an upstream region. Briefly, HEK cells were transfected with human VDR expression vector (pCMX-VDR) and expression vectors for VDR responsive luciferase (Sppx3-tk-LUC) and β-galactosidase by the calcium phosphate method. Eight hours later, compounds were added to the cells. After culturing for 16-24 hr, cells were harvested, and the activities of luciferase and β-galactosidase were measured. Luciferase activity values were corrected with β-galactosidase activity values.

Figure 2:
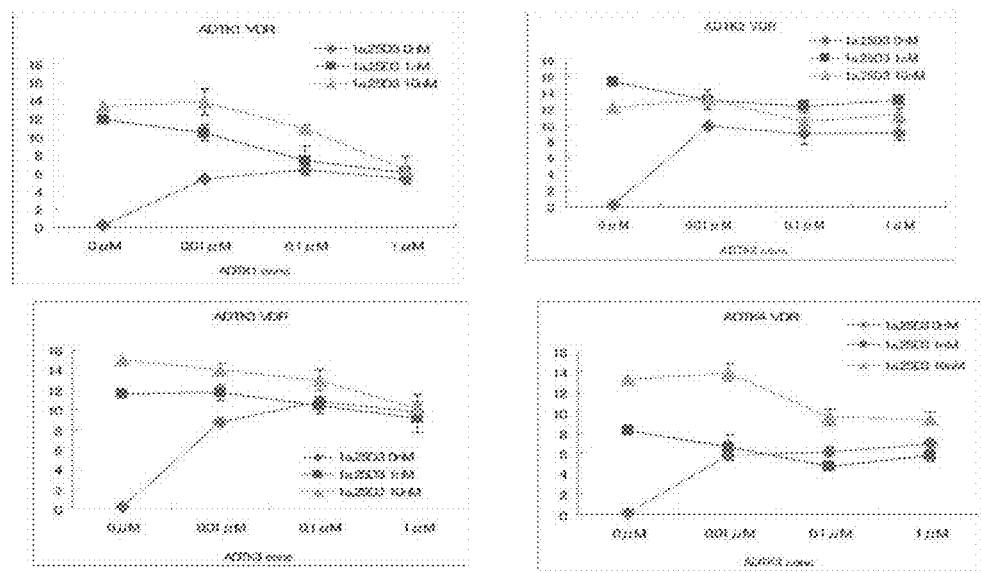
FIG. 2 shows the VDR transcription induction activity of ADTK1 through ADTK4. VDR transcription induction activity was evaluated using human embryonic kidney (HEK) 293 cells by a luciferase (Luc) assay with a Luc reporter having mouse osteopontin vitamin D response element (VDRE) (SPP) in an upstream region. ADTK2, which showed the highest VDR binding activity, already showed the highest activity at $10^{-8}$ M that was the lowest concentration used in the experiment. However, its efficacy was 66% of that of the natural hormone and did not increase further at higher concentrations. These results demonstrate that ADTK2 is a partial agonist. The other compounds (ADTK1, ADTK3 and ADTK4) showed the highest activity at concentrations around $10^{-7}$ M. Their efficacies were ADTK1: 40%, ADTK3: 72% and ADTK4: 54%. These compounds already inhibited the activity of $1,25(OH)_2D_3$ even at 10-fold concentration. At 1000-fold concentration, their activities converged at their highest activity values. That is, these compounds exhibited partial agonist and antagonist activities.

The results are shown in FIG. 2. ADTK2, which showed the highest VDR binding activity, already showed the highest activity at $10^{-8}$ M that was the lowest concentration used in the experiment. However, its efficacy was 66% of that of the natural hormone and did not increase further at higher concentrations. These results demonstrate that ADTK2 is a partial agonist. The other compounds (ADTK1, ADTK3 and ADTK4) showed the highest activity at concentrations around $10^{-7}$ M. Their efficacies were ADTK1: 40%, ADTK3: 72% and ADTK4: 54%. These compounds already inhibited the activity of $1,25(OH)_2D_3$ even at 10-fold concentration. At 1000-fold concentration, their activities converged at their highest activity values. That is, these compounds exhibited partial agonist and antagonist activities.

To summarize the results of Examples 2 and 3, each of the compounds ADTK1 through ADTK4 exhibited partial agonist activity. The $EC_{50}$ value of transcription activity well-correlated with VDR binding ability. ADTK2 exhibited the highest activity at the lowest concentration, but its efficacy did not correlate with VDR binding ability. For example, ADTK3 that showed the lowest VDR binding ability showed the highest efficacy of 72%. Each of the compounds ADTK1 through ADTK4 is a VDR partial agonist/antagonist, and a possibility that these compounds would function as tissue-selective VDR modulators was strongly shown.

Example 4

Synthesis of ADYW1 and ADYW2

(1) Synthesis of Compound 11a

Compound 11a was synthesized according to the following scheme.

[Formula 10]

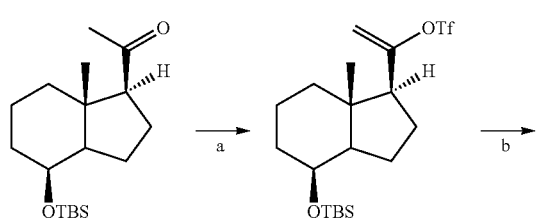

-continued

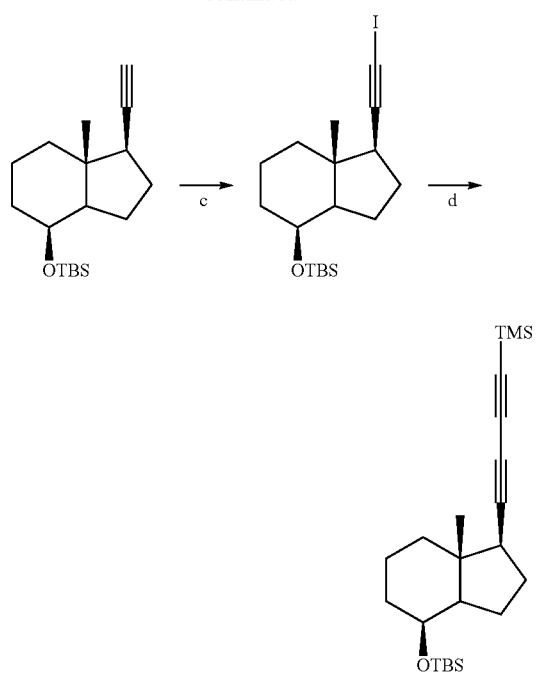

Experimental Operations (a) LDA, N-(5-chloro-2-pyridyl)-triflimide. (b) LDA, THF, rt. (c) n-HexLi, THF, $I_2$, −78° C. (d) TMS-acetylene, CuI, pyrrolidine.

CD ring alcohol protected compound 11a

11a: $^1$H NMR (CDCl$_3$)™: 0.006 (3H, s), 0.013 (3H, s), 0.179 (9H, s), 0.883 (9H, s), 1.036 (3H, s), 4.02 (1H, m)

$^{13}$C NMR (CDCl$_3$) d: −4.905, −4.510, −0.228, 14.437, 16.145, 17.801, 18.289, 23.026, 23.606, 26.077, 28.312, 29.757, 30.092, 31.978, 34.676, 38.480, 43.749, 44.559, 51.931, 68.185, 69.055, 81.377, 83.201, 89.149.

Subsequently, (25R)- and (25S)-25-(1-adamantyl)-1α,25-dihydroxy-2-methylene-20,20,22,22,23,23,24,24-octadehydro-19,21,26,27-tetranorvitamin D3 (ADYW1 and ADYW2) were synthesized according to the following scheme.

[Formula 11]

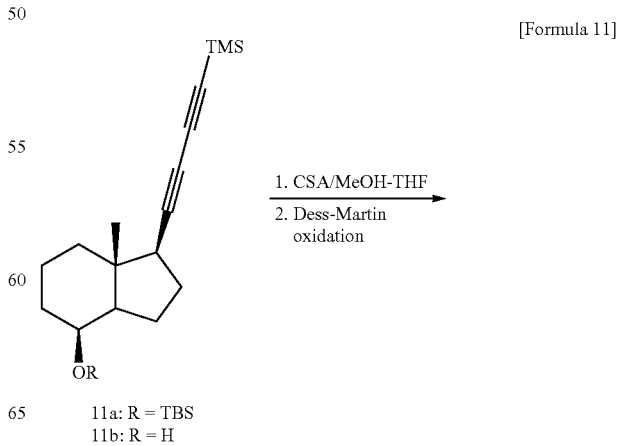

11a: R = TBS
11b: R = H

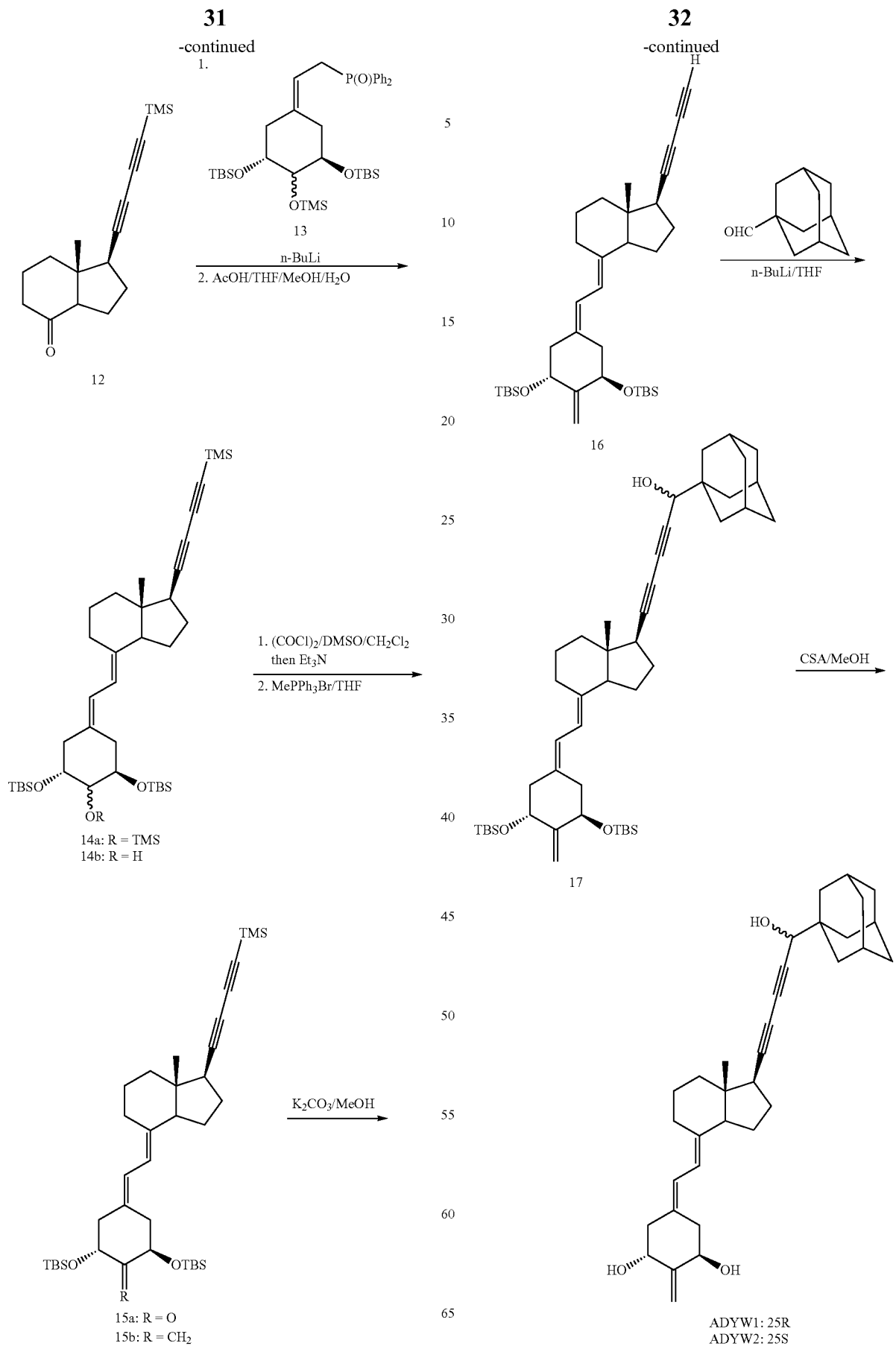

(2) Synthesis of CD Ring Alcohol Form 11b

The raw material for CD ring (11a) (20.4 mg, 0.0514 mmol) was dissolved in tetrahydrofuran (50 µL). Then, methanol (50 µL) was added thereto, followed by cooling to 0° C. A methanol solution of camphorsulfonic acid (60.6 mg, 0.257 mmol, 5 eq.) (100 µL) was added thereto, followed by stirring for 30 min. The resultant solution was returned to room temperature. Methanol (150 µL) and tetrahydrofuran (50 µL) were then added to completely dissolve the solid matter deposited in the flask, followed by stirring for 48 hr. An aqueous solution of sodium hydrogencarbonate was added to the resultant solution, followed by extraction with ethyl acetate. The organic layer was washed with saturated brine, dried over anhydrous magnesium sulfate and evaporated. The residue was purified by column chromatography ($SiO_2$, 1 g) to obtain alcohol form 11b (11.2 mg, 79.3%) from 5% ethyl acetate/hexane elution part.

11b: $^1$H-NMR ($CDCl_3$) δ: 0.18 (9H, s, TMS), 1.07 (3H, s, —CH3), 1.25 (2H, m), 1.49 (3H, m), 1.78 (5H, m), 2.04 (1H, m), 2.24 (1H, m), 4.28 (1H, m).

(3) Synthesis of CD Ring Fragment Ketone Form 12

To a solution of alcohol form 11b (54.9 mg, 0.200 mmol) in anhydrous dichloromethane (1.5 mL), Dess-Martin reagent (170.9 mg, 0.400 mmol, 2 eq.) was added as such, followed by stirring at room temperature for 2 hr. An aqueous sodium sulfite solution and an aqueous sodium hydrogencarbonate solution were then added, followed by extraction with ethyl acetate. The organic layer was washed with saturated brine, dried over anhydrous magnesium sulfate and evaporated. The residue was purified by column chromatography ($SiO_2$, 2 g) to obtain ketone form 12 (49.1 mg, 90.1%) as a CD ring fragment from 5% ethyl acetate/hexane elution part.

12: $^1$H-NMR ($CDCl_3$) δ: 0.19 (9H, s, TMS), 0.77 (3H, s, —CH3), 1.57 (2H, m), 1.77 (1H, m), 1.98 (5H, m), 2.29 (3H, m), 2.58 (1H, t, J=9.6 Hz).

(4) Synthesis of Coupling Form 14a

A solution of phosphine form 13 (42.0 mg, 0.0635 mmol, 1.3 eq.) as an A ring fragment in anhydrous tetrahydrofuran (390 µL) was cooled to −78° C. Ten minutes later, n-butyllithium (39 µL, 0.0635 mmol, 1.3 eq.) was added dropwise, followed by stirring at the same temperature for 10 min. Then, a solution of ketone form 12 (13.3 mg, 0.0488 mmol) as a CD ring fragment in anhydrous tetrahydrofuran (170 µL) was added dropwise, followed by stirring at the same temperature for 1.5 hr. The mixture was then warmed up to room temperature over 1 hr, followed by stirring at room temperature for another 1 hr. Saturated aqueous ammonium chloride solution was then added, followed by extraction with ethyl acetate. The organic layer was washed with saturated brine, dried over anhydrous magnesium sulfate and evaporated. The residue was purified by column chromatography ($SiO_2$, 2 g) to obtain coupling form 14a (17.4 mg, 50.0%) as a 4:3 mixture of A ring position 2 isomers from 1% ethyl acetate/hexane elution part.

14a: $^1$H-NMR ($CDCl_3$) δ: 0.05 (12H, m, SiMe×4), 0.12 (9H, s, TMS), 0.18 (9H, s, TMS), 0.67, 0.68 (4:3, 3 H, s, —$CH_3$), 0.87 (18H, m, t-Bu×2), 1.66 (7H, m), 2.03 (5H, m), 2.41 (4H, m), 2.82 (1H, m), 3.57 (1H, m), 3.87 (2H, m), 5.79, 5.81 (4:3, 1H, d, J=11.6 Hz), 6.08, 6.11 (3:4, 1H, d, J=11.6 Hz).

(5) Position 2 Alcohol Form 14b

The coupling form 14a (43.5 mg, 0.0610 mmol) was dissolved in tetrahydrofuran (366 µL) and cooled to 0° C. A mixture of acetate/methanol/water (8:1:1, 366 µL) was added, followed by stirring for 1 hr. Then, the resultant solution was warmed up to room temperature and stirred for 48 hr. Aqueous 5% sodium hydrogencarbonate was then added, followed by extraction with ethyl acetate. The organic layer was washed with saturated brine, dried over anhydrous magnesium sulfate and evaporated. The residue was purified by column chromatography ($SiO_2$, 1 g) to obtain alcohol form 14b (32.9 mg, 84.1%) as a 5:4 mixture of A ring 2-isomers from 0.5% ethyl acetate/hexane elution part.

14b: $^1$H-NMR ($CDCl_3$) δ: 0.08 (12H, m, SiMe×4), 0.18 (9H, s, TMS), 0.67, 0.68 (5:4, 3 H, s, —$CH_3$), 0.87 (18H, m, t-Bu×2), 1.81 (10H, m), 2.39 (5H, m), 2.82 (1H, m), 3.56 (1H, m), 3.95 (2H, m), 5.80 (1H, d, J=11.8 Hz), 6.13, 6.16 (4:5, 1H, d, J=11.8 Hz).

(6) Synthesis of Position 2 Ketone Form 15a

To a solution of oxalyl dichloride (6 µL, 0.0644 mmol, 2.4 eq.) in anhydrous dichloromethane (104 µL) cooled to −78° C., a solution of dimethyl sulfoxide (9.2 µL, 0.129 mmol, 4.8 eq.) in anhydrous dichloromethane (39 µL) was added dropwise. After stirring for 10 min, a solution of the alcohol form 14b (17.2 mg, 0.0268 mmol) in anhydrous dichloromethane (140 µL) was added dropwise. After stirring for 15 min at the same temperature, triethylamine (39 µL, 0.268 mmol, 10 eq.) was added, followed by stirring for another 30 min at the same temperature. Then, the resultant solution was warmed up to 0° C. over 1 hr, followed by stirring at that temperature for another 1 hr. Ice water was added to the solution, which was then extracted with dichloromethane. The organic layer was washed with aqueous 5% hydrochloric acid solution, saturated aqueous sodium hydrogencarbonate solution and saturated brine in this order, dried over anhydrous magnesium sulfate and evaporated. The residue was purified by column chromatography ($SiO_2$, 2 g) to obtain position 2 ketone form 15a (11.5 mg, 67.1%) from 0.5% ethyl acetate/hexane elution part.

15a: $^1$H-NMR ($CDCl_3$) δ: 0.07 (12H, m, SiMe×4), 0.18 (9H, s, TMS), 0.68 (3H, m, —$CH_3$), 0.87, 0.89 (each 9H, s, t-Bu), 1.70 (7H, m), 2.03 (5H, m), 2.44 (4H, m), 2.70 (2H, m), 2.85 (1H, m), 4.34 (1H, dd, J=6.0, 4.0 Hz), 4.55 (1H, dd, J=8.8, 5.6 Hz), 5.81 (1H, d, J=11.2 Hz), 6.33 (1H, d, J=11.2 Hz).

(7) Synthesis of Position 2 Methylene Form 15b

A solution of methyltriphenylphosphonium bromide (25.3 mg, 0.0701 mmol, 4 eq.) in anhydrous tetrahydrofuran (200 µL) was cooled to 0° C. To this solution, n-butyllithium (42 µL, 0.0701 mmol, 4 eq.) was added. After stirring for 15 min, a solution of the ketone form 15a (11.2 mg, 0.0175 mmol) in anhydrous tetrahydrofuran (130 µL) was added thereto dropwise, followed by stirring at the same temperature for 1 hr. The resultant mixture was warmed up to room temperature, followed by stirring for another 1 hr. Ice water was added to the reaction mixture, which was then extracted with ethyl acetate. The organic layer was washed with saturated brine, dried over anhydrous magnesium sulfate and evaporated. The residue was purified by column chromatography ($SiO_2$, 2 g) to obtain position 2 methylene form 15b (7.1 mg, 63.6%) from 20% dichloromethane/hexane elution part.

15b: $^1$H-NMR ($CDCl_3$) δ: 0.05 (12H, m, SiMe×4), 0.18 (9H, s, TMS), 0.68 (3H, s, —$CH_3$), 0.86, 0.90 (each 9H, s, t-Bu), 1.71 (6H, m), 2.05 (5H, m), 2.30 (1H, m), 2.47 (3H, m), 2.85 (1H, m), 4.43 (1H, m), 4.92, 4.98 (each 1H, s), 5.84 (1H, d, J=11.2 Hz), 6.20 (1H, d, J=11.2 Hz).

(8) Synthesis of Acetylene Form 16

To a solution of the position 2 methylene form 15b (19.2 mg, 0.0301 mmol) in tetrahydrofuran/methanol (1:0.7, 630 μL), potassium carbonate (21.0 mg, 0.151 mmol, 5 eq.) was added. The mixture was stirred at room temperature for 24 hr. Saturated aqueous ammonium chloride solution was added to the reaction mixture at 0° C., followed by extraction with ethyl acetate. The organic layer was washed with saturated brine, dried over anhydrous magnesium sulfate and evaporated. The residue was purified by column chromatography ($SiO_2$, 2 g) to obtain acetylene form 16 (11.7 mg, 68.7%) from 15% dichloromethane/hexane elution part.

16 $^1$H-NMR ($CDCl_3$) δ: 0.02, 0.05, 0.06, 0.08 (each 3H, s, SiMe×4), 0.68 (3H, s, —$CH_3$), 0.86, 0.90 (each 9H, s, t-Bu), 2.01 (1H, m), 2.09 (1H, m), 2.18 (1H, dd, J=12.4, 8.4 Hz), 2.30 (1H, m), 2.47 (3H, m), 2.85 (1H, m), 4.43 (1H, m), 4.92, 4.98 (each 1H, m), 5.84 (1H, d, J=11.2 Hz), 6.20 (1H, d, J=11.2 Hz).

(9) Synthesis of Adamantane Compound 17

A solution of the acetylene form 16 (11.7 mg, 0.02071 mmol) in anhydrous tetrahydrofuran (414 μL) was cooled to 0° C. To this solution, n-butyllithium (65 μL, 0.104 mmol, 5 eq.) was added. After stirring for 10 min at the same temperature, a solution of 1-formyl adamantane (15.4 mg, 0.0938 mmol, 4.5 eq.) in anhydrous tetrahydrofuran (220 μL) was added dropwise. The mixture was stirred at the same temperature for 1 hr. Saturated aqueous ammonium chloride solution was added to the reaction mixture, which was then extracted with ethyl acetate. The organic layer was washed with saturated brine, dried over anhydrous magnesium sulfate and evaporated. The residue was purified by column chromatography ($SiO_2$, 2 g) to obtain adamantine compound 17 (10.8 mg, 71.5%) from 3% ethyl acetate/hexane elution part.

17 $^1$H-NMR ($CDCl_3$) δ: 0.02, 0.05, 0.06, 0.08 (each 3H, s, SiMe×4), 0.68 (3H, s, —$CH_3$), 0.86, 0.90 (each 9H, s, t-Bu), 2.09 (1H, m), 2.18 (1H, dd, J=12.4, 8.4 Hz), 2.30 (1H, m), 2.47 (3H, m), 2.85 (1H, m), 3.00 (1H, m), 3.92 (1H, d), 4.43 (1H, m), 4.92, 4.98 (each 1H, m), 5.84 (1H, d, J=11.2 Hz), 6.20 (1H, d, J=11.2 Hz).

(10) Synthesis of (25R)- and (25S)-25-(1-Adamantyl)-1α,25-dihydroxy-2-methylene-20,20,22,22,23,23,24-octadehydro-19,21,26,27-tetranorvitamin $D_3$ (ADYW1 and ADYW2)

To a methanol solution of the adamantane compound 17 (2.00 mg, 0.00274 mmol) (1 mL), a methanol solution of camphorsulphonic acid (20.7 mg, 0.0892 mmol, 30 eq.) (200 μL) was added at 0° C. After stirring at room temperature for 1 hr, saturated aqueous sodium hydrogencarbonate solution was added to the reaction mixture, which was then extracted with ethyl acetate. The organic layer was washed with saturated brine, dried over anhydrous magnesium sulfate and evaporated. The residue was purified by column chromatography (Sephadex™ LH-20, 1 g) to obtain a mixture of the target compounds ADYW1 and ADYW2 quantitatively from chloroform/hexane/methanol (70:30:1) elution part.

ADYW1, 2 $^1$H-NMR ($CDCl_3$) δ: 0.68 (3H, s, —$CH_3$), 2.09 (1H, m), 2.45 (1H, m), 2.58 (1H, m), 2.84 (2H, dd, J=12.8, 4.4 Hz), 3.92 (1H, s), 5.01, 5.12 (each 1H, m), 5.89 (1H, d, J=11.4 Hz), 6.34 (1H, d, J=11.4 Hz).

Example 5

Synthesis of ADKM1 and ADKM2

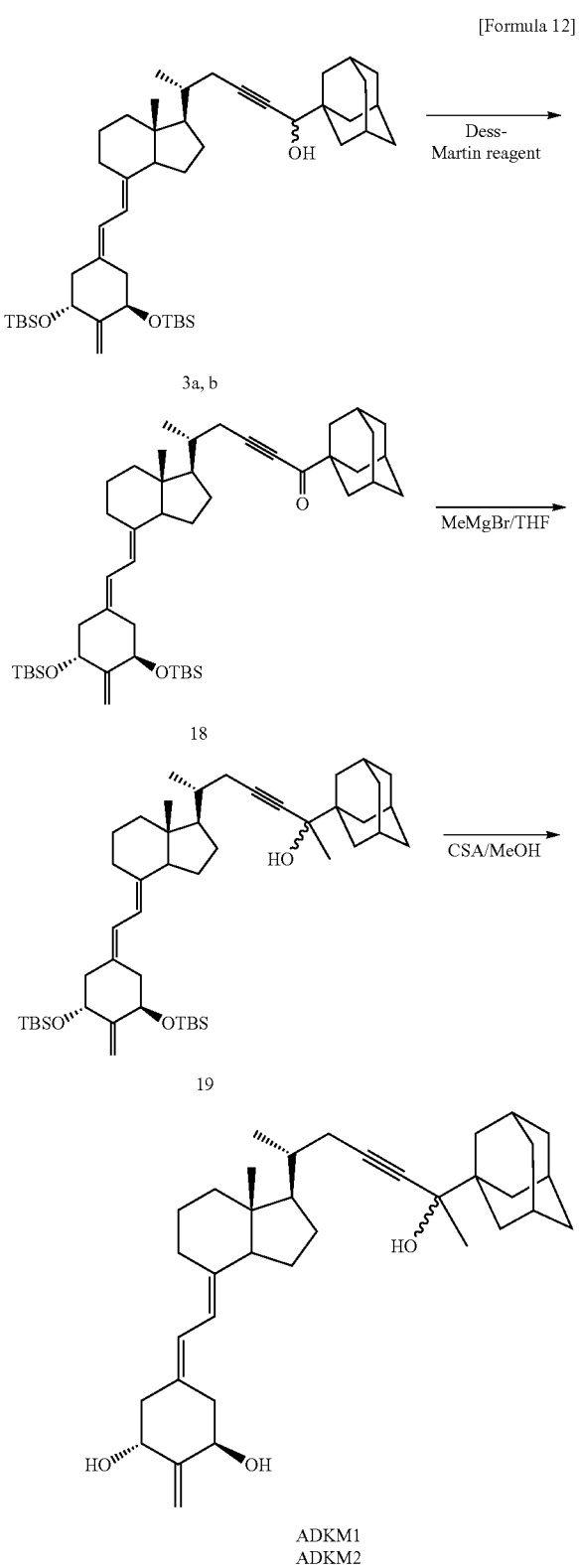

[Formula 12]

(1) Synthesis of Ketone Form 18

To a dichloromethane solution of TBS ether form 3 (11.6 mg, 0.016 mmol) (300 μl), Dess-Martin reagent (15.5 mg, 0.037 mmol, 2 eq) was added, followed by stirring at room temperature for 2 hr. 1 M aqueous sodium sulfite solution and saturated sodium hydrogencarbonate solution were added to the reaction mixture, followed by extraction with dichloromethane. The organic layer was washed with saturated brine, dried over anhydrous magnesium sulfate and evaporated. The residue was purified by column chromatography ($SiO_2$, 5.5 g) to obtain ketone form 18 (5.4 mg, 46.7%) from 3% ethyl acetate/hexane elution part.

18: $^1$H NMR ($CDCl_3$) δ 0.03, 0.05, 0.07, 0.08 (each 3H, s), 0.57, (3H, s), 0.87, 0.90 (each 9H, s), 1.14 (3H, d, J=6.8 Hz), 4.92 (1H, s) 4.98 (1H, s) 5.85 (1H, d, J=11.0 Hz) 6.21 (1H, d, J=11.0 Hz)

(2) Synthesis of 25-Methyl Form 19

To a solution of the ketone form 18 (5.4 mg, 7.3 mmol) in anhydrous THF (60 μL), a THF solution of methylmagnesium bromide (29.0 μl, 29 μmol, 4 eq) was added under argon gas flow at 0° C. and stirred for 30 min. Then, the mixture was stirred at room temperature for 2 hr. Subsequently, saturated ammonium chloride was added to the reaction mixture, followed by extraction with ethyl acetate. The organic layer was washed with saturated brine, dried over anhydrous magnesium sulfate and evaporated. The residue was purified by column chromatography ($SiO_2$, 6.3 g) to obtain methylated form 19 (2.8 mg, 50.8%) as a mixture of 25-epimers from 3% ethyl acetate/hexane elution part.

19: $^1$H NMR ($CDCl_3$) δ 0.03, 0.05, 0.07, 0.08 (each 3H, s), 0.56, (3H, s), 0.86, 0.90 (each 9H, s), 1.10 (3H, d, J=6.4 Hz), 1.39 (3H, s), 4.92 (1H, s) 4.97 (1H, s) 5.84 (1H, d, J=11.0 Hz), 6.21 (1H, d, J=11.0 Hz)

(3) Synthesis of (25R)- and (25S)-25-(1-Adamantyl)-1α,25-dihydroxy-2-methylene-23,23,24,24-tetradehydro-19,27-dinorvitamin $D_3$ (ADKM1 and ADKM2)

To a methanol solution of the methylated form (2.8 mg, 3.7 mmol) (2.8 ml), a methanol solution of camphorsulfonic acid (5.1 mg, 22.0 μmol, 6 eq) (400 μl) was added at 0° C. The mixture was stirred at room temperature for 8 hr. Saturated aqueous sodium hydrogencarbonate solution was added to the reaction mixture, which was then extracted with ethyl acetate. The organic layer was washed with saturated brine, dried over anhydrous magnesium sulfate and evaporated. The residue was purified by column chromatography (Sephadex™ LH-20, 1.5 g) to obtain ADKM1 and ADKM2 (1.0 mg, 50.1%) as a mixture of 25-epimers from chloroform/hexane/methanol (70:30:1) elution part.

ADKM: $^1$H NMR ($CDCl_3$) δ 0.57, (3H, s), 1.10 (3H, d, J=6.4 Hz), 1.39 (3H, s), 5.10 (1H, s) 5.11 (1H, s) 5.90 (1H, d, J=11.4 Hz) 6.36 (1H, d, J=11.4 Hz).

UV (95% EtOH) λmax 245, 253 and 263 nm

Formulation Example 1

Thirty grams of ADK2, 140 g of crystalline cellulose, 100 g of lactose, 15 g of cellulosic calcium glycolate, 10 g of hydroxypropylcellulose, and 30 ml of purified water are charged into a kneader and kneaded for 5 minutes by a conventional method. After kneading, the obtained product is sieved through a 10-mesh screen and dried in a drier at 50° C. After drying, the product is granulated and 5 g of magnesium stearate is added to the granulation. After mixing for 1 min, the resultant mixture is compressed into tablets each having a weight of about 100 mg and a diameter of 6.5 mm. Each tablet contains 10 mg of ADK2.

All publications, patents and patent applications cited herein are incorporated herein by reference in their entirety.

INDUSTRIAL APPLICABILITY

The present invention is applicable to prevention and/or treatment of diseases in which a vitamin D receptor is involved, more specifically, osteoporosis, malignant neoplasms (e.g., myeloid leukemia, breast cancer, prostate cancer, colon cancer, etc.), psoriasis vulgaris, autoimmune diseases (e.g., chronic rheumatoid arthritis, systemic lupus erythematosus, etc.), infectious diseases (e.g., tuberculosis, etc.), neurodegenerative diseases (e.g., multiple sclerosis, etc.), disorders in glucose/lipid metabolism, cardiovascular diseases, and the like.

The invention claimed is:

1. A compound represented by the following formula (I),

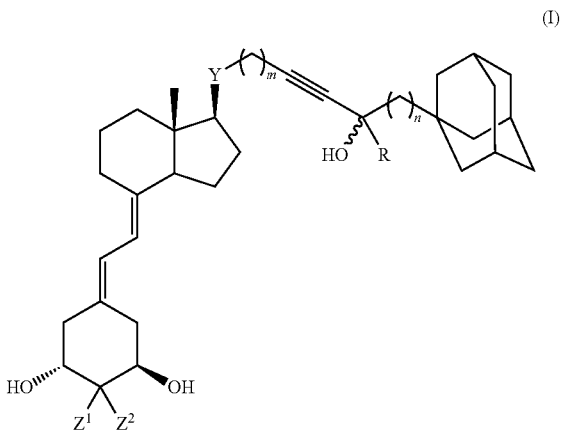

(I)

wherein m and n each independently represent 1 or 0;
R represents a hydrogen atom or an alkyl group;
Y represents an ethane-1,1-diyl group or an ethyne-1,2-diyl group; and
Z1 represents a hydrogen atom and Z2 represents a hydroxyalkoxy group, or Z1 and Z2 jointly form a methylene group.

2. The compound according to claim 1, wherein the compound represented by the formula (I) is selected from the group consisting of (25S)-25-(1-Adamantyl)-1α,25-dihydroxy-2-methylene-23,23,24,24-tetradehydro-19,26,27-trinorvitamin $D_3$, (25R)-25-(1-Adamantyl)-1α,25-dihydroxy-2-methylene-23,23,24,24-tetradehydro-19,26,27-trinorvitamin $D_3$, (25R)-26-(1-Adamantyl)-1α,25-dihydroxy-2-methylene-23,23,24,24-tetradehydro-19,27-dinorvitamin $D_3$, (25S)-26-(1-Adamantyl)-1α,25-dihydroxy-2-methylene-23,23,24,24-tetradehydro-19,27-dinorvitamin $D_3$, (25R)-25-(1-Adamantyl)-1α,25-dihydroxy-2-methylene-20,20,22,22,23,23,24,24-octadehydro-19,21,26,27-tetranorvitamin $D_3$, (25S)-25-(1-Adamantyl)-1α,25-dihydroxy-2-methylene-20,20,22,22,23,23,24,24-octadehydro-19,21,26,27-tetranorvitamin $D_3$, (25R)-25-(1-Adamantyl)-1α,25-dihydroxy-2-methylene-23,23,24,24-tetradehydro-19,27-dinorvitamin $D_3$ and (25S)-25-(1-Adamantyl)-1α,25-dihydroxy-2-methylene-23,23,24,24-tetradehydro-19,27-dinorvitamin $D_3$.

3. A composition comprising the compound according to claim 1.

* * * * *

UNITED STATES PATENT AND TRADEMARK OFFICE
CERTIFICATE OF CORRECTION

PATENT NO. : 9,018,194 B2
APPLICATION NO. : 14/002502
DATED : April 28, 2015
INVENTOR(S) : Makoto Makishima et al.

Page 1 of 1

It is certified that error appears in the above-identified patent and that said Letters Patent is hereby corrected as shown below:

Title page,

Item (73) Assignee:

"Nibon University" should read "Nihon University."

Signed and Sealed this
Thirteenth Day of October, 2015

Michelle K. Lee
*Director of the United States Patent and Trademark Office*